US008877928B2

(12) United States Patent
Song et al.

(10) Patent No.: US 8,877,928 B2
(45) Date of Patent: Nov. 4, 2014

(54) PEGYLATED CYCLOPAMINE ANALOGUE, PREPARATION METHOD AND USES THEREOF

(75) Inventors: Chun Song, Shandong (CN); Chengzhi Zhang, Beijing (CN); Xin Zhao, Beijing (CN); Zhao Hu, Beijing (CN); Xiuling Xu, Beijing (CN); Youzhong Zhang, Beijing (CN); Mingyi Wang, Beijing (CN); Zhijun Sun, Beijing (CN)

(73) Assignee: Shandong University, Beijing (CN)

( * ) Notice: Subject to any disclaimer, the term of this patent is extended or adjusted under 35 U.S.C. 154(b) by 0 days.

(21) Appl. No.: 13/882,797

(22) PCT Filed: Feb. 25, 2011

(86) PCT No.: PCT/CN2011/000303
§ 371 (c)(1),
(2), (4) Date: Aug. 16, 2013

(87) PCT Pub. No.: WO2011/103773
PCT Pub. Date: Sep. 1, 2011

(65) Prior Publication Data
US 2013/0324569 A1 Dec. 5, 2013

(30) Foreign Application Priority Data

Feb. 26, 2010 (CN) .......................... 2010 1 0114769

(51) Int. Cl.
A61K 31/133 (2006.01)
C08G 65/333 (2006.01)
C08L 71/00 (2006.01)
A61P 35/00 (2006.01)
A61K 47/48 (2006.01)

(52) U.S. Cl.
CPC ......... *A61K 47/48215* (2013.01); *A61K 31/133* (2013.01); *C08G 65/33396* (2013.01); *C08L 2203/02* (2013.01)
USPC ............... 546/41; 546/15; 546/198; 514/278; 514/279; 514/299

(58) Field of Classification Search
USPC .............................................. 514/279; 546/41
See application file for complete search history.

(56) References Cited

U.S. PATENT DOCUMENTS

| 7,230,004 | B2 * | 6/2007 | Adams et al. ................. 514/278 |
| 2008/0107749 | A1 | 5/2008 | Maitra et al. |
| 2008/0248097 | A1 | 10/2008 | Kwon et al. |
| 2008/0248126 | A1 | 10/2008 | Cheng et al. |
| 2011/0064752 | A1 | 3/2011 | Hutchinson et al. |

OTHER PUBLICATIONS

Dorwald; "Side Reactions in Organic Synthesis: A Guide to Successful Synthesis Design" 2005 Wiley-VCH Verlag GmbH & Co. KGaA, Wienheim, chapter 1.*
International Search Report mailed Jun. 9, 2011, for PCT/CN2011/000303.
International Preliminary Report on Patentability mailed Aug. 28, 2012, for PCT/CN2011/000303.

* cited by examiner

*Primary Examiner* — John Mabry
*Assistant Examiner* — Daniel Carcanague
(74) *Attorney, Agent, or Firm* — Banner & Witcoff, Ltd.

(57) ABSTRACT

A PEGylated cyclopamine analog, preparation method, uses thereof and methods for treating proliferative diseases using the same are disclosed. The PEGylated cyclopamine analog is a compound represented by the following formula I, a compound comprising at least one group represented by the following formula I (in formula I, R is straight or branched polyethylene glycol having a molecular weight between 200 and 200,000 Dalton, L and X are linking groups), or their single enantiomers, mixture of enantiomers, mixture of diastereomers, pharmaceutically acceptable salts, solvates, or hydrates.

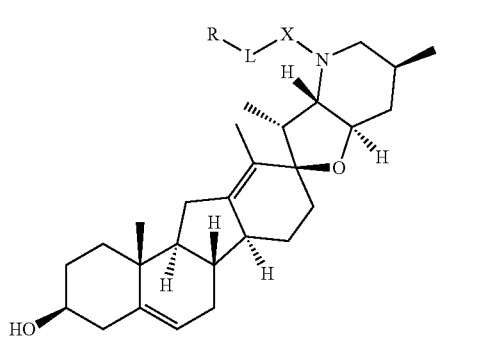
(I)
16 Claims, 2 Drawing Sheets

PEGYLATED CYCLOPAMINE ANALOGUE, PREPARATION METHOD AND USES THEREOF

This application is a U.S. National Stage application of co-pending PCT application PCT/CN2011/000303 filed Feb. 25, 2011, which claims the priority of Chinese application 201010114796.8, filed Feb. 26, 2010, each application being incorporated by reference in their entirety.

TECHNICAL FIELD

The present invention provides PEGylated cyclopamine analogs as Hedgehog pathway inhibitors, pharmaceutical compositions comprising the compounds, and preparation method of the same. The present invention also provides a method of using the compounds for the treatment of proliferative diseases.

BACKGROUND ART

Hedgehog (Hh) signaling pathway is a pathway that is ancient and in highly conservative development, and it participates in the embryo formation of most tissues and maintains and repairs mature tissues in the adult body. The members of the hedgehog family in secreted proteins control cell proliferation, differentiation and tissue formation. Hh signal in the adult body is significantly reduced as compared with those in embryo and newborn body. Inappropriate Hh pathway is activated in certain types of cancers. The cancers include, for example, basal cell carcinoma (Ervin H. Epstein (2008) *Nat Rev Cancer.* 8: 743-54), medulloblastoma (Raffel, C. (1997) *Cancer Research.* 57: 842-845), small cell lung cancer (Watkins, D. N. et al (2003) *Nature* 422, 313-317), pancreatic cancer (Thayer, S. P. et al. (2003) *Nature* 425, 851-856), prostate tumor (Karhadkar, S. S., et al. (2004) *Nature* 431, 707-712), and chronic lymphocytic leukemia (Hegde, C. V. et al (2008) *Mol Cancer Res.* 6 (12): 1928-36). Therefore, the inhibition of abnormal Hh signaling pathway is a remarkable target to the design of anticancer drug.

Hedgehog gene was first identified in Drosophila. The mutation of Hh results in abnormal spike covering the back of the larvae, developing to prompt Hedgehog (Nusslein-Volhard, C. et al. 1980, *Nature* 287, 795-801). In mammalian cells, three Hedgehog genes, Sonic hedgehog (Shh), Indian hedgehog (Ihh) and Desert hedgehog (Dhh) have been identified (Echelard, Y. et al; *Cell* 1993, 75, 1417-1430). Shh is the most common hedgehog member in mammals, and is also the preferably characterized ligand in hedgehog family. Prior to secretion, Shh undergoes intramolecular cleavage and lipid modification reaction. The lipid-modified peptide is the cause for the activation of all signals. Two transmembrane proteins are involved in signal transduction of Hh pathway: twelve-transmembrane Patched receptor (PTCH), and seven-transmembrane Smoothened protein (Smo), which act as important positive medium for Hh signaling. The three Hh proteins are used as ligands to start Hh signaling. The receptor of Hh pathway is Ptch, twelve-pass transmembrane protein). When lacking Hh ligand, Ptch binds G-protein that is coupled with receptor-like signal transduction smoothing factor (Smo), and blocks its function (Eggenschwiler, J. T. (2007) *Annu. Rev. Cell Dev. Biol.* 23, 345-373). The binding with Hh ligand reduces the inhibitory effect of Ptch-mediated Smo. Upon binding Hh ligand, the inhibition of Ptch on Smo is reduced. Then, Smo is activated, and starts signaling cascade, the signaling cascade leading to the activation of inscriptional factors Gli1-3 (Alexandre et al (1996) *Genes Dev.* 10: 2003-13), which regulates Hh target genes including cyclin D, cyclin E (Duman-Scheel, M. et al (2002) *Nature* 417, 299-304), c-myc (Ingham P W et al. *Genes Dev* 2001; 15(23): 3059-87) and Bcl2 (Regl, G. et al. (2004) *Cancer Res.* 64, 7724-7731). The pathway is an important regulator of cell cycle and differentiation during development.

In the past decade, it is increasingly evident that the abnormal expression of Hh pathway members will lead to the formation and maintenance of cancer. It has been reported that a number of genes (for example, Shh, PTCH1, Smo and Gli) promote the development of different cancers. PTCH1 is the first Hh network gene associated with cancer. The patient with genetic negative mutant PTCH (which may cause constitutive activation of Hh signaling) has a high incidence of basal cell carcinoma and medulloblastoma (Johnson, R. L. et al (1996) *Science* 272, 1668-1671, Epstein, E. H. (2008) *Nat. Rev. Cancer* 8, 743-754). The haploinsufficiency of the two genes PTCH and SUFU is associated with rhabdomyosarcoma especially fetal rhabdomyoma and embryonic rhabdomyosarcoma (Tostar, U. et al. (2006), *J. Pathol.* 208, 17-25). The mutation of Smo or Ptch1 in cerebellar neurons, which leads to constitutive activation of Smo, usually may cause medulloblastoma (Vorechovsky, I. et al. (1997) *Oncogene* 15, 361-366). It has been found that, compared to that in healthy cells, the transcriptional level of Smo, Gli1 and Ptch1 in oncogenic multiple myeloma cells upregulates significantly. Because Hh pathway is generally involved in cancer, the method of blocking this pathway is highly interesting. It has been shown that the inhibition of the Hedgehog pathway activity with small molecules will cause cell death in many different types of cancers with uncontrolled hedgehog pathway activation.

Among hedgehog pathway inhibitors, cyclopamine (a plant veratrine) is quite interesting. Cyclopamine directly binds Smo, and acts as an antagonist of the Hh pathway. Animal trials verified that cyclopamine exhibited anti-tumor activity in a number of models of small cell lung cancer, medulloblastoma, prostate cancer and gastrointestinal cancer. Despite of its attractive pharmacological properties, the use of cyclopamine for systemic treatment may be subjected to the following restrictions: 1) teratogenic, including: loss of midline facial features, uniocular, lack of anatomical features from forebrain; 2) poorly water-soluble (5 µg/mL); and 3) chemically instable at low pH (Chen. J. K., al. (2002), *Proc. Natl. Acad. Sci. U.S.A*, 99, 14071-14076).

CONTENTS OF THE INVENTION

Summary of the Invention

The object of the present invention is to provide a cyclopamine derivative which has excellent characteristics including good solubility and/or enhanced pH stability, and can be used in clinical application for the treatment of various diseases. The present inventors surprisingly found that, by coupling polyethylene glycol with cyclopamine to obtain a PEGylated cyclopamine analog, the above object of the present invention was achieved successfully. Based on the above findings, the present invention has been completed.

To this end, a first aspect of the present invention is to provide a PEGylated cyclopamine analog, which is a compound represented by the following formula I, or a compound comprising at least one moiety which is the same as or different from each other represented by the following formula I:

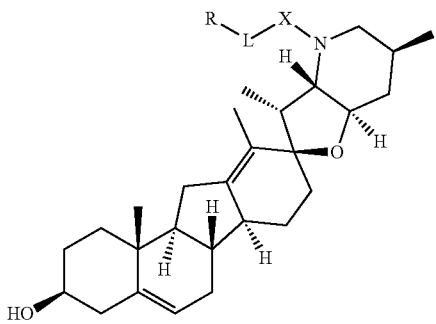

(I)

or a single enantiomer thereof, a mixture of enantiomers, or a mixture of diastereomers, or a pharmaceutically acceptable salt, a solvate, or a hydrate thereof, wherein:

R is straight or branched polyethylene glycol having a molecular weight of 200 to 200,000 Dalton, L is a linking group represented by the following formula II:

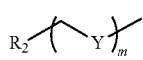

(II)

wherein $R_2$ is selected from the group consisting of —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$ N$R^f R^g$, —N$R^f R^g$, —N$R^e$C(O)$R^h$, —N$R^e$C(O)O$R^f$, —N$R^e$C(O)N$R^f R^g$, —N$R^e$C(=N$R^h$)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S$R^e$, —S(O)$R^e$, —S(O)$_2 R^e$, —S(O)N$R^f R^g$ and —S(O)$_2$ N$R^f R^g$, wherein $R^e$, $R^f$, $R^g$ and $R^h$ are each independently selected from the group consisting of hydrogen, $C_{1-6}$ alkyl and $C_{2-6}$ alkenyl, or $R^f$ and $R^g$ together with the N atom to which they are attached form a nitrogen-containing heterocyclic group;

Y is selected from the group consisting of O, N, S—S, methylene and ethylidene, which optionally comprises the following other functional groups: tissue-specific target functional groups and/or various cell-specific target functional groups such as vitamins, folic acid derivatives, antibodies;

m is an integer of 0-6; specifically, m is 0, 1, 2, 3, 4, 5 or 6;

X is a linking group between cyclopamine and L, which is selected from the group consisting of —C(O), —OC(O), —NC(O), —OS(O), —OS(O)$_2$ and —OS(O).

The PEGylated cyclopamine analog according to any item of the first aspect of the present invention is characterized in that the polyethylene glycol as represented by R has a molecular weight of 300 to 180,000 Dalton, 400 to 160,000 Dalton, 500 to 150,000 Dalton, 600 to 120,000 Dalton, 800 to 100,000 Dalton, 1,000 to 80,000 Dalton, 1,500 to 60,000 Dalton, 2,000 to 50,000 Dalton, 5,000 to 50,000 Dalton, 7,500 to 50,000 Dalton, or 10,000 to 50,000 Dalton.

The PEGylated cyclopamine analog according to any item of the first aspect of the present invention is characterized in that the polyethylene glycol as represented by R is polyethylene glycol represented by the following formula III:

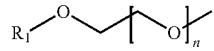

(III)

wherein:

$R_1$ is a terminating group, which is selected from the group consisting of H, Me, alkyl (e.g. $C_{1-12}$ alkyl, $C_{1-8}$ alkyl, $C_{1-6}$ alkyl, or $C_{1-4}$ alkyl), tissue-specific target functional groups and/or various cell-specific target functional groups such as vitamins, folic acid derivatives, antibodies;

n at each occurrence is independently an integer of 100 to 4500 (for example, an integer of 100-4000, or an integer of 100-3500, or an integer of 100-3000, or an integer of 100-2500, or an integer of 100-2000, or an integer of 100-1500, or an integer of 100-1000, or an integer of 100-800, or an integer of 100-500. In one embodiment, n is an integer of 120-4500, or an integer of 150-4500, or an integer of 200-4500 or an integer of 250-4500, or an integer of 300-4500, or an integer of 350-4500, or an integer of 500-4500, or an integer of 800-4500, or an integer of 1000-4500 or an integer of 1200-4500, or an integer of 1500-4500, or an integer of 2000-4500 or an integer of 2500-4500, or an integer of 3000-4500. In one embodiment, n is an integer of 120-4200, or an integer of 150-4000, or an integer of 200-3500, or an integer of 250-3000, or an integer of 300-2500, or an integer of 350-2000, or an integer of 500-2000, or an integer of 800-1500).

The PEGylated cyclopamine analog according to any item of the first aspect of the present invention is characterized by any one or more of the following items (1)-(3):

(1) R is straight or branched polyethylene glycol having a molecular weight of 200 to 200,000 Dalton (e.g., 300 to 180,000 Dalton, 400 to 160,000 Dalton, 500 to 150,000 Dalton, 600 to 120,000 Dalton, 800 to 100,000 Dalton, 1000 to 80,000 Dalton, 1,500 to 60,000 Dalton, 2,000 to 50,000 Dalton, 5,000 to 50,000 Dalton, 7,500 to 50,000 Dalton, or 10,000 to 50,000 Dalton), (2) L is a linking group represented by the following formula II:

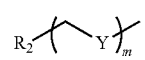

(II)

wherein, $R_2$ is selected from the group consisting of —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$ N$R^f R^g$, —N$R^f R^g$, —N$R^e$C(O)$R^h$, —N$R^e$C(O)O$R^f$, —N$R^e$C(O)N$R^f R^g$, —N$R^e$C(=N$R^h$)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S$R^e$, —S(O)$R^e$, —S(O)$_2 R^e$, —S(O)N$R^f R^g$ and —S(O)$_2$N$R^f R^g$, wherein $R^e$, $R^f$, $R^g$ and $R^h$ are each independently selected from the group consisting of hydrogen, $C_{1-6}$ alkyl and $C_{2-6}$ alkenyl, or $R^f$ and $R^g$ together with the N atom to which they are attached form a nitrogen-containing heterocyclic group;

Y is selected from the group consisting of O, N, S—S, methylene and ethylidene, which optionally comprises the following other functional groups: tissue-specific target functional groups and/or various cell-specific target functional groups such as vitamins, folic acid derivatives, antibodies;

m is an integer of 0-6; specifically, m is 0, 1, 2, 3, 4, 5 or 6.

(3) X is a linking group between cyclopamine and L, which is selected from the group consisting of —C(O), —OC(O), —NC(O), —OS(O), —OS(O)$_2$ and —OS(O).

In the present invention, the term "vitamin" includes vitamins A, vitamins B, vitamin C, vitamin D, vitamin E, and the like.

The second aspect of the present invention is to provide a method for preparing the PEGylated cyclopamine analog according to any item of the first aspect of the present invention, which comprises the following steps:

i) providing polyethylene glycol or a derivative thereof, or their functionalized products such as carboxylated products, amidated products, and derivatives or protected forms thereof;

ii) reacting the substance provided in step i) with cyclopamine or a single enantiomer thereof, a mixture of enantiomers, or a mixture of diastereomers, or a pharmaceutically acceptable salt, a solvate, or a hydrate thereof to obtain a PEGylated cyclopamine analog, and, optionally, iii) subjecting the PEGylated cyclopamine analog obtained in step ii) to further treatment such as separation, crystallization, purification, salification, solvation and the like.

A third aspect of the present invention is to provide a pharmaceutical composition comprising a therapeutically and/or prophylactically effective amount of the PEGylated cyclopamine analog according to any item of the first aspect of the present invention, or a single enantiomer thereof, a mixture of enantiomers, or a mixture of diastereomers, or a pharmaceutically acceptable salt, a solvate, or a hydrate thereof, and optionally one or more pharmaceutically acceptable carriers or excipients.

The fourth aspect of the present invention is to provide use of the PEGylated cyclopamine analog according to any item of the first aspect of the present invention or of the pharmaceutical composition according to any item of the third aspect of the present invention in the preparation of a medicament for the treatment and/or prevention of proliferative diseases, neoplastic diseases or cancer diseases. In the use according to the fourth aspect of the present invention, the proliferative diseases, neoplastic diseases or cancer diseases are diseases that can be treated and/or prevented with cyclopamine or an analogue thereof. Specifically, the neoplastic diseases or cancer diseases are lung cancer, ovarian cancer, prostate cancer, liver cancer, or breast cancer.

A fifth aspect of the present invention is to provide a method of treating and/or preventing proliferative diseases, neoplastic diseases or cancer diseases in a mammal in need, which comprises administering to the mammal in need a therapeutically and/or prophylactically effective amount of the PEGylated cyclopamine analog according to any item of the first aspect of the present invention or the pharmaceutical composition according to any item of the third aspect of the present invention. In the method according to the fifth aspect of the present invention, the proliferative diseases, neoplastic diseases or cancer diseases are diseases that can be treated and/or prevented with cyclopamine or an analogue thereof. Specifically, the neoplastic diseases or cancer diseases are lung cancer, ovarian cancer, prostate cancer, liver cancer, or breast cancer.

A sixth aspect of the present invention is to provide use of the PEGylated cyclopamine analog according to any item of the first aspect of the present invention or of the pharmaceutical composition according to any item of the third aspect of the present invention as the Hedgehog pathway inhibitor.

DETAILED DESCRIPTION OF THE INVENTION

The PEGylated cyclopamine analog according to the first aspect of the present invention is a coupled product obtained by linking polyethylene glycol or a derivative thereof to cyclopamine via ring nitrogen atom in F ring of cyclopamine, or a single enantiomer thereof, a mixture of enantiomers, or a mixture of diastereomers, or a pharmaceutically acceptable salt, a solvate, or a hydrate thereof. The chemical structure of cyclopamine and the serial numbers of its six fused rings A-F are shown as follows:

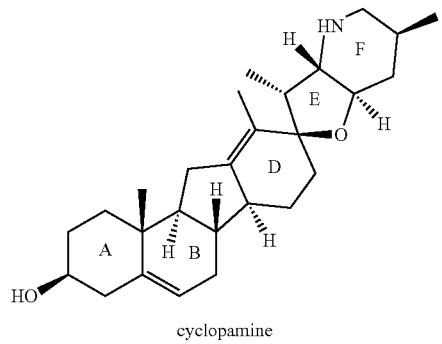

cyclopamine wherein the hydrogen atom attached to the ring nitrogen atom in F ring of cyclopamine is substituted by polyethylene glycol or a derivative thereof via an optional linker, thereby forming the PEGylated cyclopamine analog according to any item of the first aspect of the present invention.

In the PEGylated cyclopamine analog according to any item of the first aspect of the present invention, the polyethylene glycol or the derivative thereof is linked to cyclopamine via a linker comprising an amide group, a sulfamide group, or sulfinyl amide group. In one embodiment, the linker comprises a group selected from the group consisting of —C(O), —OC(O), —NC(O), —OS(O), —OS(O)$_2$, and —OS(O). In one embodiment, the linker comprises a moiety represented by the following formula II:

(II)

wherein R$_2$, Y and m are as described in the present invention.

The PEGylated cyclopamine analog according to the first aspect of the present invention is a compound represented by the following formula I, or a compound comprising at least one moiety which is the same as or different from each other represented by the following formula I:

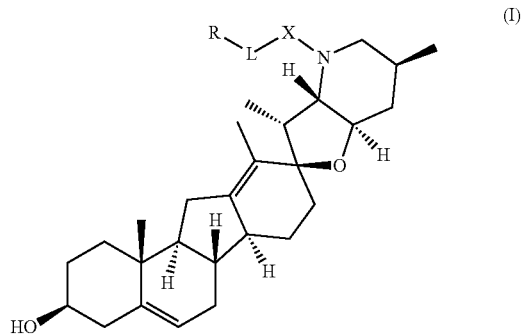

(I)

or a single enantiomer thereof, a mixture of enantiomers, or a mixture of diastereomers, or a pharmaceutically acceptable salt, a solvate, or a hydrate thereof, wherein:

R is water-soluble functionalized polyethylene glycol having different structures, the polyethylene glycol being straight or branched and having a molecular weight of 200 to 200,000 Dalton. R as described herein is represented by the following formula III:

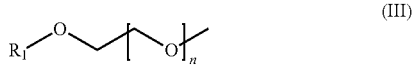

(III)

wherein:

$R_1$ is a terminating group, which comprises H, Me, alkyl, tissue-specific target functional groups and/or various cell-specific target functional groups such as vitamins, folic acid derivatives, antibodies; n is the number of ethylene glycol units, which at each occurrence is independently an integer of 110 to 4,500, and represents water-soluble PEG having a molecular weight of 200 to 200,000 Dalton, L is a covalent bond, and is preferably a biodegradable linking group having different molecular lengths between R and X. L described herein is represented by the following formula II:

(II)

wherein, $R_2$ is selected from the group consisting of —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$N$R^f R^g$, N$R^f R^g$, —N$R^e$C(O)$R^h$, —N$R^e$C(O)O$R^f$, —N$R^e$C(O)N$R^f R^g$, —N$R^e$C(=N$R^h$)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S$R^e$, —S(O)$R^e$, —S(O)$_2 R^e$, —S(O)N$R^f R^g$ and —S(O)$_2$N$R^f R^g$, wherein $R^e$, $R^f$, $R^g$ and $R^h$ are each independently selected from (i) hydrogen; (ii) $C_{1-6}$ alkyl, $C_{2-6}$ alkenyl; or (iii) $R^f$ and $R^g$ together with the N atom to which they are attached form a nitrogen-containing heterocyclic group;

Y is selected from the group consisting of O, N, S—S, methylene and ethylidene, which optionally comprises the following other functional groups: tissue-specific target functional groups and/or various cell-specific target functional groups such as vitamins, folic acid derivatives, antibodies;

m is the number of alkylene linkers, which is an integer of 0-6;

X is preferably a biodegradable linking group between cyclopamine and L, which is selected from the group consisting of —C(O), —OC(O), —NC(O), —OS(O), —OS(O)$_2$ and —OS(O).

In the PEGylated cyclopamine analog according to any item of the first aspect of the present invention, the polyethylene glycol or a derivative thereof is a straight or branched polyethylene glycol or a derivative thereof.

In the PEGylated cyclopamine analog according to any item of the first aspect of the present invention, the polyethylene glycol or a derivative thereof has a number of ethylene glycol units, n, which is an integer of 100 to 4500 (for example, an integer of 100-4000, or an integer of 100-3500, or an integer of 100-3000 or an integer of 100-2500, or an integer of 100-2000, or an integer of 100-1500, or an integer of 100-1000 or an integer of 100-800, or an integer of 100-500. In one embodiment, n is an integer of 120-4500, or an integer of 150-4500, or an integer of 200-4500, or an integer of 250-4500, or an integer of 300-4500, or an integer of 350-4500 or an integer of 500-4500, or an integer of 800-4500, or an integer of 1000-4500, or an integer of 1200-4500 or an integer of 1500-4500 or an integer of 2000-4500, or an integer of 2500-4500 integer, or an integer of 3000-4500. In one embodiment, n is an integer of 120-4200, or an integer of 150-4000 or an integer of 200-3500 or an integer of 250-3000, or an integer of 300-2500, or an integer of 350-2000, or an integer of 500-2000, or an integer of 800-1500 or an integer of 1-100).

In the PEGylated cyclopamine analog according to any item of the first aspect of the present invention, the polyethylene glycol or a derivative thereof has a molecular weight of 200-200,000 Dalton (e.g., 300 to 180,000 Dalton, 400 to 160,000 Dalton, 500 to 150,000 Dalton, 600 to 120,000 Dalton, 800 to 100,000 Dalton, 1000 to 80,000 Dalton, 1500 to 60,000 Dalton, 2000 to 50,000 Dalton, 5000 to 50,000 Dalton, 7500 to 50,000 Dalton, or 10,000 to 50,000 Dalton).

In one embodiment, the PEGylated cyclopamine analog described herein is selected from the group consisting of:

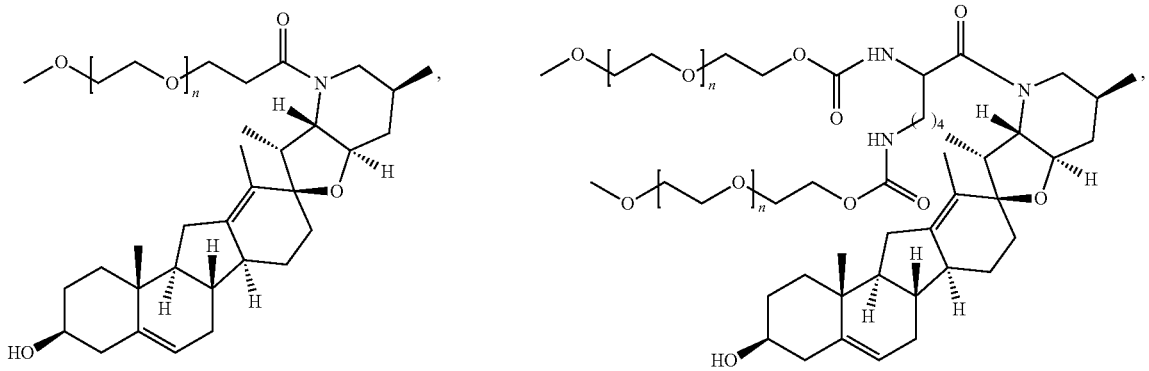

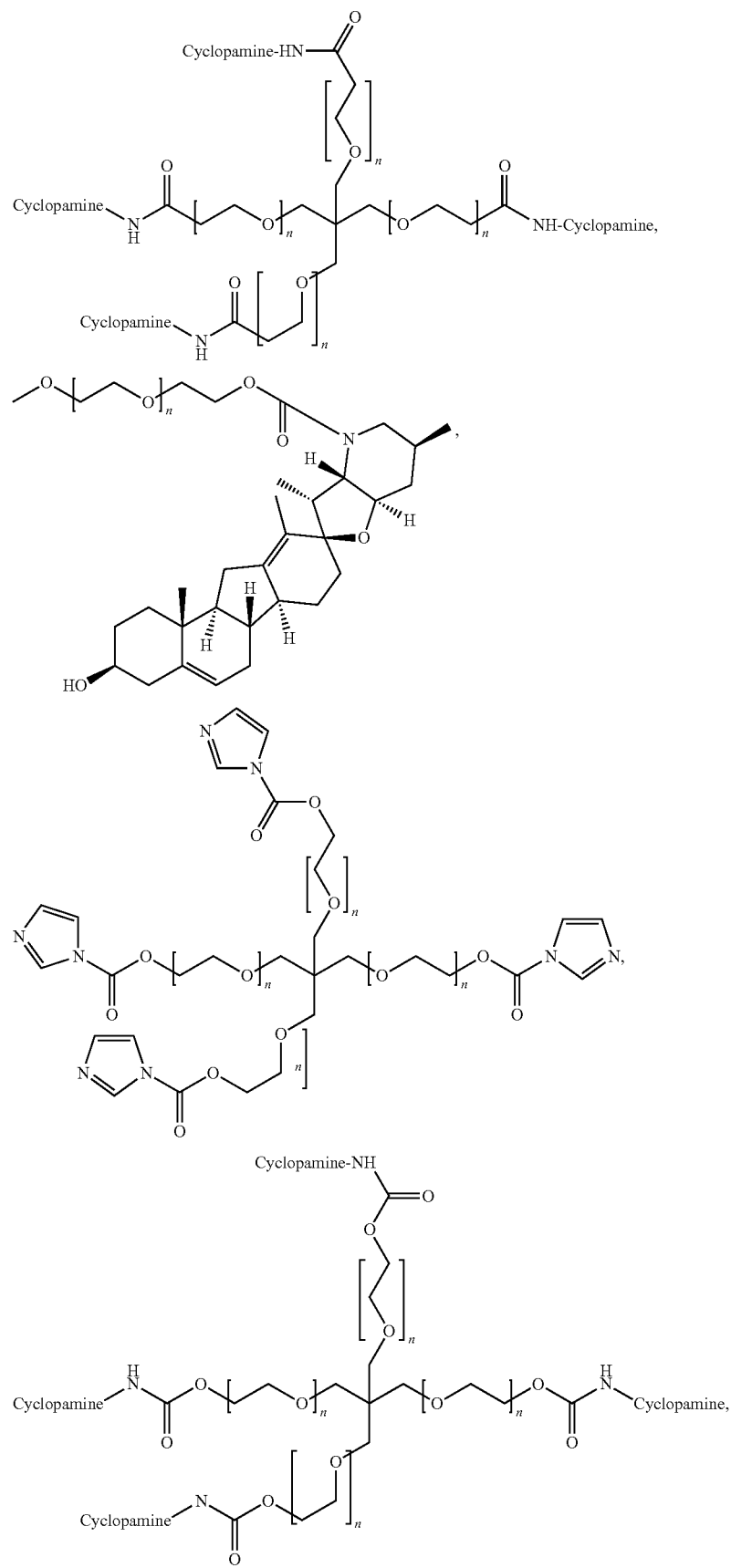

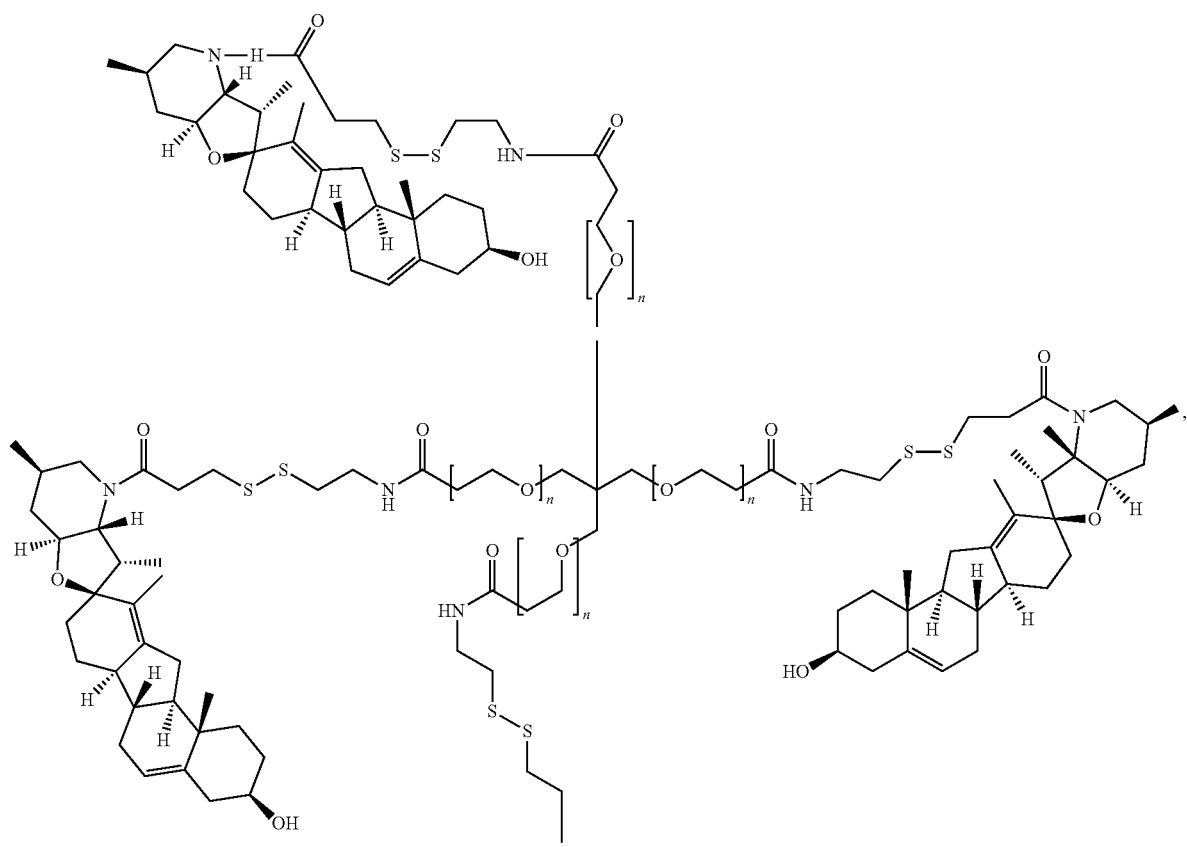
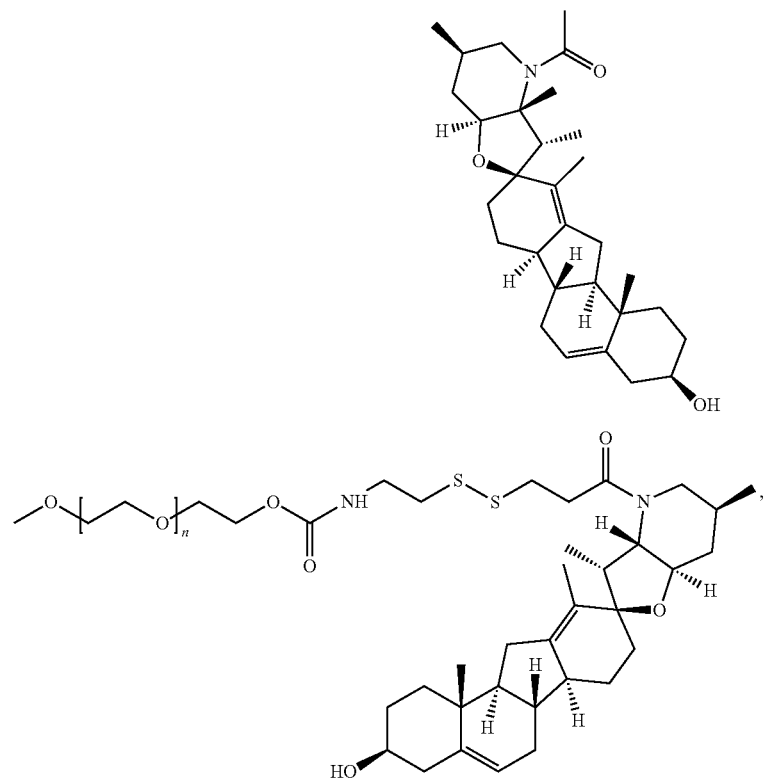

-continued
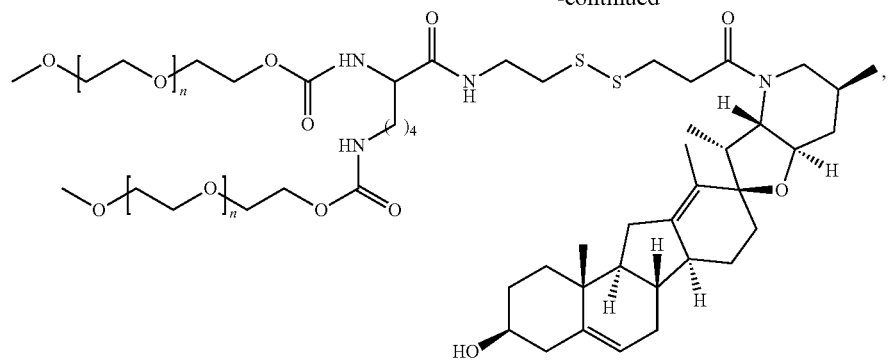
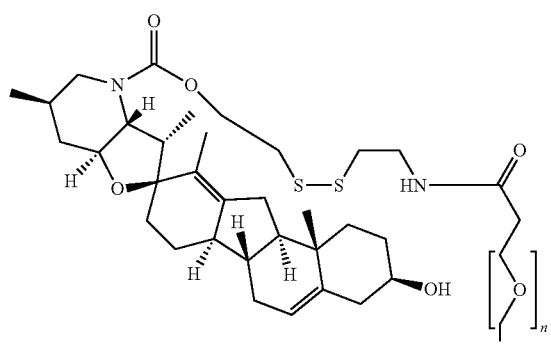
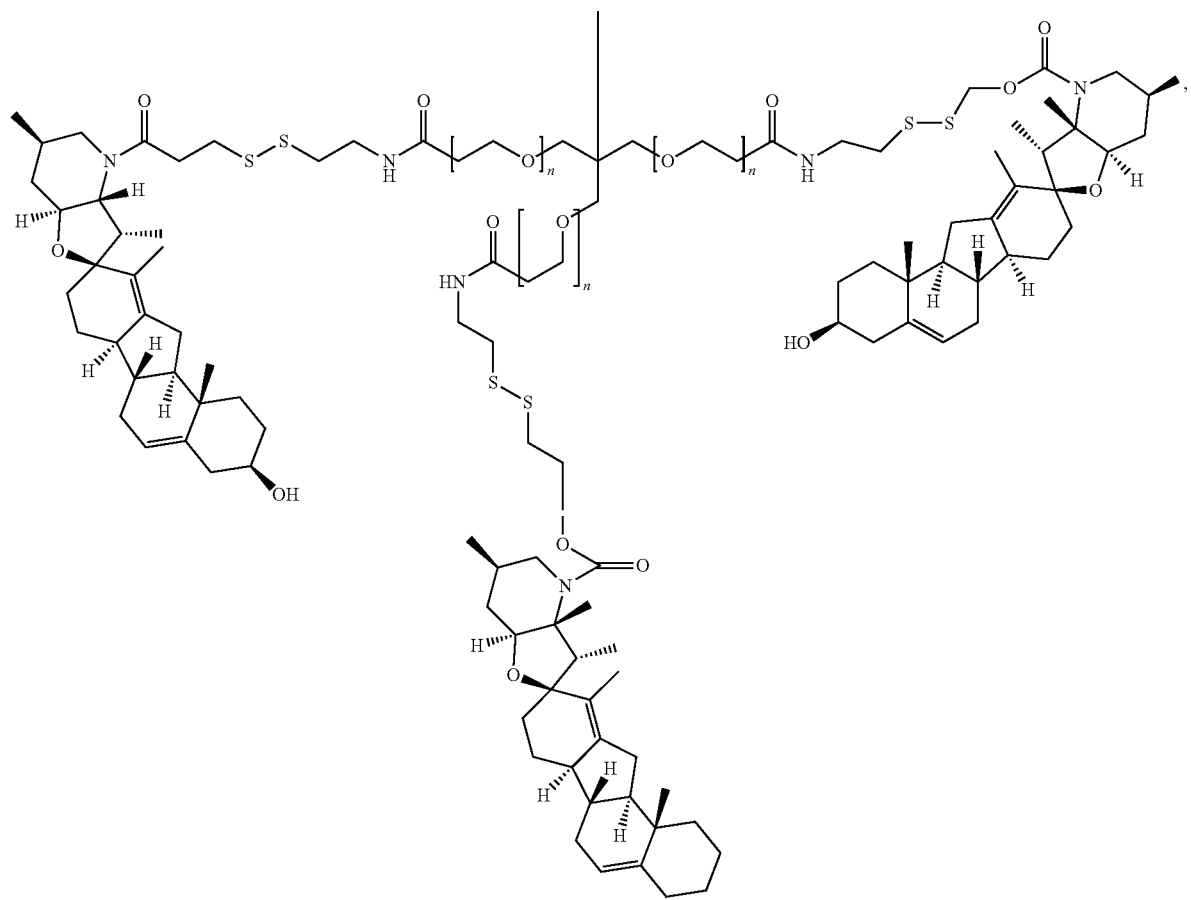

and a pharmaceutically acceptable salt, solvate and hydrate thereof.

The various aspects and features of the present invention are further described below.

As to all references cited in the present invention, the entire contents thereof are incorporated herein by reference, and, if the meanings expressed by these references are inconsistent with those given in the present invention, those given in the present invention shall be adopted. In addition, various terms and phrases used in the invention have the general meanings as well known to a person skilled in the art. Even so, it is still wished in the present invention that more detailed descriptions and explanations are given for these terms and phrases. If the meanings of some terms and phrases as given in the present invention are inconsistent with their known meanings, those given in the present invention shall be adopted.

The term "alkyl", "alkenyl" and "alkynyl" used herein have the general meanings as well known in the art. They are straight or branched hydrocarbon groups, and these groups typically have a carbon number of 1-22, e.g. 1-20, 1-15, 1-12, 1-10, 1-8, 1-6, or 1-4. Of course, as to "alkenyl" and "alkynyl", their carbon numbers are at least two. Examples of these groups include, but are not limited to, methyl, ethyl, propyl, isopropyl, n-butyl, sec-butyl, tert-butyl, allyl, propenyl, propynyl group and the like. Moreover, said "alkyl", "alkenyl" and "alkynyl" may be collectively referred to as "hydrocarbyl" or "chain hydrocarbon group".

As used herein, the phrase "$C_1$-$C_6$ alkyl" refers to substituted or unsubstituted alkyl group having the specified carbon number, for example, $C_1$-$C_4$ alkyl, $C_1$-$C_3$ alkyl group, $C_1$-$C_2$ alkyl. Examples of "$C_1$-$C_6$ alkyl" include, but are not limited to: methyl, ethyl, propyl, isopropyl, butyl, tert-butyl, pentyl, neopentyl group.

As used herein, the phrase "cycloalkyl" refers to cyclic alkyl group containing 3-10, 3-8, 3-6, or 3-5 carbon atoms, which may optionally contain 1-3 ring heteroatom selected from nitrogen, oxygen, or sulfur, and at this time, it may be referred to as a heterocyclic alkyl group or a heterocyclic group. In addition, cycloalkyl group may optionally contain double bond(s). Examples of "cycloalkyl" include, but are not limited to, "$C_3$-$C_8$ cycloalkyl group", which refers to substituted or unsubstituted cycloalkyl group having the specified carbon number, for example, $C_3$-$C_6$ cycloalkyl, $C_3$-$C_5$ cycloalkyl, such as cyclopropyl, cyclobutyl, cyclopentyl or cyclohexyl group.

The present invention also relates to suitable pharmaceutically acceptable salt, solvate or hydrate of the PEGylated cyclopamine analog according to the first aspect of the present invention, wherein the pharmaceutically acceptable salt includes, but is not limited to, the salts formed by the PEGylated cyclopamine analog according to the first aspect of the present invention with various inorganic acids such as hydrochloric acid, sulfuric acid, phosphoric acid, phosphorous acid, hydrobromic acid and nitric acid, and with various organic acids such as maleic acid, malic acid, fumaric acid, succinic acid, tartaric acid, citric acid, acetic acid, lactic acid, methanesulfonic acid, p-toluenesulfonic acid, palmitic acid and the like. Some compounds of the present invention may be crystallized or recrystallized with water or various organic solvents. In this case, various solvates may be formed. The present invention includes those stoichiometric solvates, including hydrates, and also including compounds containing variable amounts of water that are formed by low pressure sublimation drying process.

The present invention also relates to various isomers of the PEGylated cyclopamine analog according to the first aspect of the present invention. Some compounds in the present invention may exist in the form of optical isomers or tautomers. The present invention includes all their existing forms, especially the form of pure isomers. Different isomeric forms can be separated or resolved from other forms of isomers by various conventional means, or certain isomers can be obtained by a variety of conventional synthetic processes or stereospecific or asymmetric synthetic processes. Since the PEGylated cyclopamine analog according to the first aspect of the present invention serves for pharmaceutical purpose, it can be understood that it is preferably provided in a pure form, for example, a purity of at least 60%, preferably 75%, more preferably 85%, most preferably at least 98% (herein, % means a percent by weight; in the present specification, a person skilled in the art understands that, the % has its well known meaning in the context where it occurs, for example, in the description of a liquid, the % usually refers to a percent by weight/volume). Impure compounds can be prepared in a purer form for use in the pharmaceutical composition. These not-so-pure products contain at least 1%, preferably 5%, more preferably at least 10%, of the PEGylated cyclopamine analog or a pharmaceutically acceptable derivative thereof according to the first aspect of the present invention.

In accordance with the detailed teachings of the present invention as well as the existing common knowledge of synthesis chemistry, a person skilled in the art could readily synthesize the PEGylated cyclopamine analog according to the first aspect of the present invention.

Further, the PEGylated cyclopamine analog or a pharmaceutically acceptable salt thereof according to the first aspect of the present invention can be used alone, or used together with a pharmaceutically acceptable carrier or excipient in the form of a pharmaceutical composition. When used in the form of a pharmaceutical composition, typically an effective amount of the PEGylated cyclopamine analog or a pharmaceutically acceptable salt or hydrate thereof according to the first aspect of the present invention is combined with one or more pharmaceutically acceptable carriers or diluents and made into a suitable administration form or dosage form. This procedure comprises mixing, granulating, compressing or dissolving the components by a suitable manner. Accordingly, the present invention provides a pharmaceutical composition, which comprises the PEGylated cyclopamine analog, any possible isomer, prodrug, pharmaceutically acceptable salt, solvate or hydrate thereof according to the first aspect of the present invention and at least one pharmaceutically acceptable carrier.

As used herein, the term "composition" is intended to include the product comprising various specified ingredients in specified amounts, and, any product obtained directly or indirectly from the combination of various specified ingredients in specified amounts. According to the present invention, the term "composition" refers to "pharmaceutical composition".

The pharmaceutical composition comprising the compound of the present invention can be administered according to any of the following routes: oral, spray inhalation, rectal, nasal, vaginal, topical, parenteral such as subcutaneous, intravenous, intramuscular, intraperitoneal, intrathecal, intraventricular, intrasternal or intracranial injection or infusion, or by means of an explanted reservoir, wherein oral, intramuscular, intraperitoneal or intravenous administration route is preferred. Further, in order to make the compound of the present invention or the pharmaceutical composition comprising the same be effective for the treatment of central nervous system diseases, intraventricular administration route is preferred so as to avoid the possible low blood brain barrier permeability of the compound.

The compound of the present invention or the pharmaceutical composition comprising the same can be administered in unit dosage form. The dosage form may be a liquid dosage form, a solid dosage form. The liquid dosage form can be true solutions, colloids, particulates, emulsions or suspensions. Other dosage forms include, for example, tablets, capsules, pills, aerosols, pills, powders, solutions, suspensions, emulsions, granules, suppository, lyophilized powder for injection, clathrate, implants, patches, liniment and the like.

The pharmaceutical composition of the present invention may further comprise commonly used carriers. The pharmaceutically acceptable carrier used herein includes, but is not limited to, ion exchangers, alumina, aluminum stearate, lecithin, serum proteins such as human serum albumin, buffer agents such as phosphates, glycerine, sorbic acid, potassium sorbate, partial glyceride mixtures of saturated vegetable fatty acid, water, salts or electrolytes, such as protamine sulfate, disodium hydrogen phosphate, potassium hydrogen phosphate, sodium chloride, zinc salts, colloidal silicon oxide, magnesium trisilicate, polyvinylpyrrolidone, cellulosic material, polyethylene glycol, sodium carboxymethylcellulose, polyacrylate, beeswax, lanolin and the like. The content of the carrier in the pharmaceutical composition can be from 1 wt %-98 wt %, usually approximately 80 wt %. For convenience, local anesthetic, preservatives, buffers and the like can be directly dissolved in the carrier.

Oral tablets and capsules can contain excipients, for example, binders such as syrup, arabic gum, sorbitol, tragacanth, or polyvinylpyrrolidone, fillers such as lactose, sucrose, corn starch, calcium phosphate, sorbitol, amino acetic acid, lubricants such as magnesium stearate, talc, polyethylene glycol, silica, disintegrating agent such as potato starch, or acceptable moistening agent such as sodium lauryl sulfate. Tablets can be coated by using methods well known in pharmaceutical chemistry.

Oral liquid can be made into water and oil suspensions, solutions, emulsions, syrups or elixirs, or can also be made into dry preparation, to which, before use, water or other suitable medium is added. Such liquid preparation can contain conventional additives such as suspending agent, sorbitol, cellulose methyl ether, glucose syrup, gel, hydroxyethyl cellulose, carboxymethyl cellulose, aluminum stearate gel, hydrogenated edible fats, emulsifiers such as lecithin, sorbitan monooleates, arabic gum; or non-aqueous carrier (which may include edible oils) such as almond oil, grease such as glycerin, ethylene glycol, or ethanol; preservatives such as methyl or propyl paraben, sorbic acid. If necessary, a flavoring or coloring agent can be added.

Suppositories can contain conventional suppository bases. The excipient therein is in a solid state at room temperature, but melts at body temperature and releases drug, which is, for example, cacao butter, other glycerides or beeswax.

For parenteral administration, the liquid dosage form is usually made of the compound and a sterilized carrier. The carrier is preferably water. According to the difference of the selected carrier and of the concentration of the drug, the compound can be dissolved in the carrier and can also be made into a suspension. When making a solution for injection, the compound is firstly dissolved in water, and then filtered and sterilized before filling in sealed bottles or ampules.

For topical administration on skin, the compound of the present invention can be made into an appropriate form of ointments, lotions, or creams, wherein the active ingredient is suspended or dissolved in one or more carriers. The carrier that can be used in ointments includes, but is not limited to, mineral oil, liquid petrolatum, white petrolatum, propylene glycol, polyoxyethylene, polyoxypropylene, emulsifying wax and water; the carrier that can be used in lotions and creams includes, but is not limited to, mineral oil, sorbitan monostearate, Tween 60, cetyl ester wax, hexadecene aryl alcohol, 2-octyldodecanol, benzyl alcohol and water.

According to the different mode of administration, the composition can comprise the active ingredient in a weight percent of 0.1%, or preferably 10-60%. However, when the composition comprises a unit dose, each unit preferably contains 1-500 mg of the active ingredient.

When used for the above-mentioned treatment and/or prevention or other treatment and/or prevention, the compound of the present invention in a therapeutically and/or prophylactically effective amount can be used in its original form, or in the form of its pharmaceutically acceptable ester or prodrug (in the case that such form is in existence). Alternatively, the compound can be administered in the form of a pharmaceutical composition comprising the compound and one or more pharmaceutically acceptable excipients. The phrase "a therapeutically and/or prophylactically effective amount" of the compound of the present invention refers to an amount of the compound that is sufficient for the treatment of disorder at a rational effect/risk ratio that is applicable to any medical treatment and/or prevention. However, it should be recognized that the total daily dose of the compound and composition of the present invention should be determined by an attending physician within a reliable scope of medical judgment. For any particular patient, the specific therapeutically effective dose level should be determined according to a variety of factors, including the disorder to be treated and the severity of said disorder; the activity of the specific compound used; the specific composition used; the patient's age, body weight, general health condition, gender and diet; the administration time, the administration route and the excretion rate of the specific compound used; the duration of treatment; the drug(s) used in combination, or simultaneously, with the specific compound; and similar factors well known in the medical field. For example, according to the practice in the art, the dose of the compound is determined by making experiment starting from a dose below the level required for achieving the desired therapeutic effect, and then gradually increasing the dose until achieving the desired effect. Generally speaking, the dose to mammal, particularly human, of the PEGylated cyclopamine analog according to the first aspect of the present invention can be in the range of 0.0001 to 1000 mg/kg body weight/day, for example, in the range of 0.001 to 100 mg/kg body weight/day, for example, in the range of 0.01 to 100 mg/kg body weight/day, for example, in the range of 0.01 to 10 mg/kg body weight/day; or, the dose to mammal, particularly human, of the PEGylated cyclopamine analog according to the first aspect of the present invention, as calculated by the amount of cyclopamine therein, can be in the range of 0.0001 to 1000 micromoles cyclopamine/kg body weight/day, for example, in the range of 0.001 to 100 micromoles cyclopamine/kg body weight/day, for example, in the range of 0.01 to 100 micromoles cyclopamine/kg body weight/day, for example, in the range of 0.01 to 10 micromoles cyclopamine/kg body weight/day. Alternatively, the dose to mammal, particularly human, of the PEGylated cyclopamine analog according to the first aspect of the present invention can be determined by referring to the dose of cyclopamine in normal use, for example, the PEGylated cyclopamine analog according to the first aspect of the present invention can be used in a dose 0.1 to 10 times, for example, 0.1 to 8 times, 0.1 to 7 times, 0.2 to 6 times, 0.2 to 5 times, or 0.2 to 2 times, that of cyclopamine in normal use.

It must be recognized that the optimal administration dose and interval of the PEGylated cyclopamine analog according to the first aspect of the present invention is determined by the property of the compound and the external conditions including the form, route and location of administration, and the like. The optimal administration dose can be determined by conventional techniques. Also it must be recognized that the optimal course of treatment, i.e., the daily dose within a predetermined time of the PEGylated cyclopamine analog according to the first aspect of the present invention, can be determined by methods well known in the art.

MODE OF CARRYING OUT THE INVENTION

Figure 1:
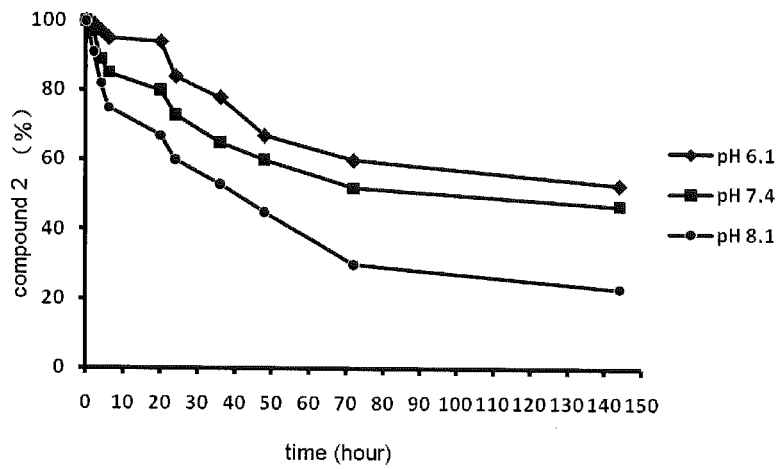
FIG. 1: A graph of the residual amount (expressed in percentage) of compound 2 at different pH values (6.1, 7.3 and 8.1) along with time (0, 2, 4, 6, 20, 24, 36, 48, 72 and 144 h).

The present invention will be further described by the following examples. However, the scope of the present invention is not limited to the following examples. A person skilled in the art can understand that, on the premise of not departing from the spirit and scope of the present invention, various changes and modifications can be made to the present invention.

The materials and experimental methods used in the experiments of the present invention are generally and/or specifically described. Although many materials and operation methods used to achieve the object of the present invention are known in the art, they are still described in the present invention as much detailed as possible.

For all of the following examples, the standard operation and purification methods known to a person skilled in the art can be used. Unless otherwise indicated, all temperatures are expressed in ° C. (degree Celsius). All reactions are carried out at room temperature, unless otherwise indicated. As for the synthesis methods, the applicable methods of organic chemistry will be exemplarily described by using specific examples, and it does not mean to limit the scope of the present invention. In addition, in the following examples, although the degree of polymerization (n) of ethylene glycol monomer of polyethylene glycol or a derivative thereof is identified in the reaction process, the specification of the polyethylene glycol or a derivative thereof is identified by its molecular weight, for example, "mPEG-NHS-20K" used in the examples represents a product wherein polyethylene glycol has a molecular weight of 20,000 Dalton. In addition, the polyethylene glycol or a derivative thereof used in the examples is commercially available, and other raw materials or reagents are self-made or commercially available.

Extraction and separation of cyclopamine: cyclopamine is derived from *Veratrum californicum* according to the scheme proposed by Keeler and collaborators.

The root samples of *Veratrum californicum* are collected. The samples are air dried, ground into fine powder, and suspended in a $CH_2Cl_2$ mixture (~6 L/kg dried particles) containing $NH_4OH$ (5%) for up to 16 hours at room temperature. The solvent is decanted, and the remainder is concentrated into a paste, which is then put in a mixture of THF/hexane (1:3). After standing for 2-3 days, the solvent is decanted, and then the remainder is concentrated into a viscous oily matter. The crude oily matter is loaded onto a silica gel column (1-2 by weight), and eluted by $EtOAc/CH_2Cl_2/MeOH/Et_3N$ (8:1:1:0.1). The fraction enriched with cyclopamine is concentrated to one quarter volume, and the precipitated cyclopamine is filtered. Further precipitation can be carried out by using acetone to obtain more cyclopamine. The merged cyclopamine can be purified by recrystallization in hot MeOH (30-40 by volume). This scheme usually results in 1 g of cyclopamine per kg of dry biomass. Cyclopamine obtained by this method typically has a RP-HPLC purity exceeding 95 a/a % @ 215 nm. (Compound 1) $^1H$ NMR (400 MHz, $CD_2Cl_2$) 5.40 (m, 1H,), 3.50 (tt, J=11.2, 4.0 Hz, 1H), 3.18 (ddd, J=10.8, 9.7, 3.9 Hz, 1H), 3.03 (ddd, J=12.4, 4.2, 1.1 Hz, 1H), 2.62 (t, J=8.8 Hz, 1H), 2.41 (p, J=7.6 Hz, 1H); 2.37 (ddd, J=10.8, 4.8, 2.2 Hz, 1H), 2.27 (m, 3H), 2.23 (m, 1H), 2.18 (m, 1H), 2.11 (m, 1H), 1.89 (m, 1H), 1.83 (m, 1H), 1.81 (m, 1H), 1.78 (m, 1H), 1.76 (m, 1H), 1.72 (m, 1H), 1.64 (s, 3H), 1.58 (m, 1H), 1.55 (m, 1H), 1.51 (m, 1H), 1.44 (m, 1H), 1.31 (m, 1H), 1.25 (m, 1H), 1.23 (m, 1H), 1.13 (m, 1H), 1.00 (s, 3H), 0.94 (d, J=5.2 Hz, 3H), 0.92 (d, J=5.6 Hz, 3H); $^{13}C$ NMR (100 MHz, $CD_2Cl_2$) δ 142.2 (C-12), 141.9 (C-5), 127.0 (C-13), 121.7 (C-6), 85.0 (C-17), 75.6 (C-23), 71.7 (C-3), 66.5 (C-22), 54.9 (C-26), 52.1 (C-9), 49.1 (C-14), 41.9 (2C, C-4 and C-8), 39.9 (C-20), 39.2 (C-24), 38.2 (C-1), 36.5 (C-10), 31.9 (C-16), 31.7 (C-25), 31.5 (C-2), 31.1 (C-7), 28.8 (C-11), 24.7 (C-15), 18.7 (C-27), 18.4 (C-19), 12.8 (C-18), 10.4 (C-21); HRMS (m/z): [M+H]+ calculated value: $C_{27}H_{42}NO_2$: 412.32101, observed value: 412.32058.

General Purification of the Final Compound:

All the synthesized PEGylated compounds are subjected to dialysis, by using a dialysis bag (MWCO XXXXX) of the corresponding specification and water (2 L), for up to 24 hours (changing water 2.0 L×3 times). Then, the solution is freeze-dried to obtain a solid compound. The solid compound is recrystallized by firstly dissolved in dichloromethane and then precipitated with ethyl ether, and thereafter dried under vacuum and 35° C., to obtain the final compound.

EXAMPLE 1

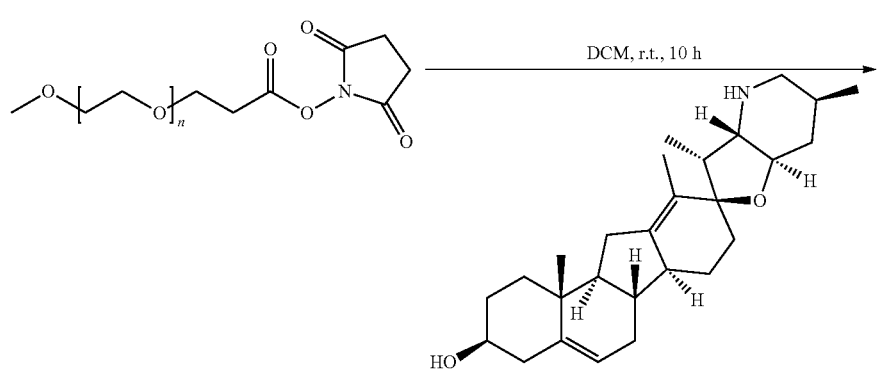

1

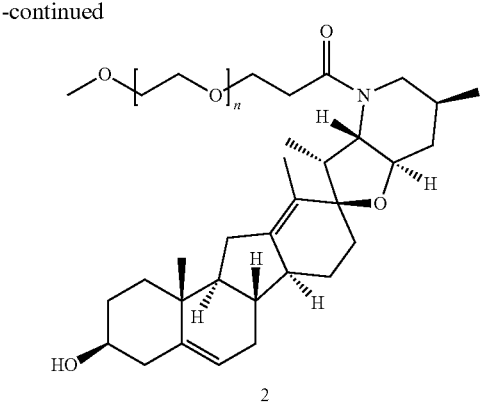

2

A mixture of mPEG-NHS-20K (1.0 g, 0.05 mmol) and cyclopamine (22.6 mg, 0.055 mmol, 1.1 equivalent of compound 1) in 10.0 mL of anhydrous dichloromethane was stirred at room temperature for 24 hours. The mixture was evaporated under a reduced pressure to about 1.5 mL, to which were then added 5.0 mL of water and a dialysis bag (MWCO 20000), and thereafter the solution was dialyzed against water (2 L) for 24 hours (changing water 2.0 L×3 times). The solution was then freeze-dried into a solid compound. The solid compound was recrystallized by firstly dissolved in dichloromethane and then precipitated with ethyl ether, and thereafter dried under vacuum and 35° C., to obtain 0.98 g of the final compound (compound 2).

$^{13}$C NMR (100 MHz, CD$_2$Cl$_2$) δ 172.31 (PEG), 142.2 (C-12), 141.9 (C-5), 127.0 (0-13), 121.7 (C-6), 85.0 (C-17), 75.6 (C-23), 71.7 (C-3), 71.15 (PEG), 69.60 (PEG), 66.30 (C-22), 61.54 (C-26), 52.1 (C-9), 49.1 (C-14), 41.9 (2C, C-4 and C-8), 39.9 (C-20), 39.2 (C-24), 38.2 (C-1), 36.5 (C-10), 31.9 (C-16), 31.7 (C-25), 31.5 (C-2), 31.1 (C-7), 28.8 (C-11), 24.7 (C-15), 18.7 (C-27), 18.4 (C-19), 12.8 (C-18), 10.4 (C-21).

EXAMPLE 2

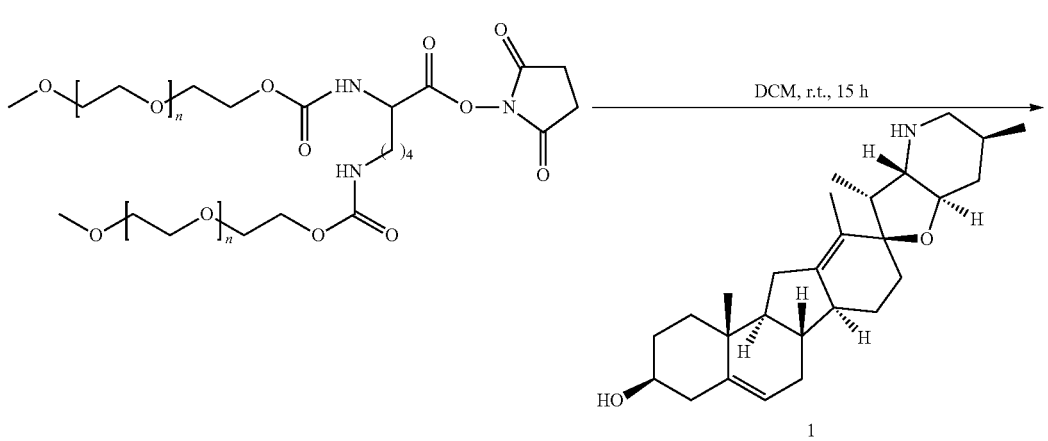

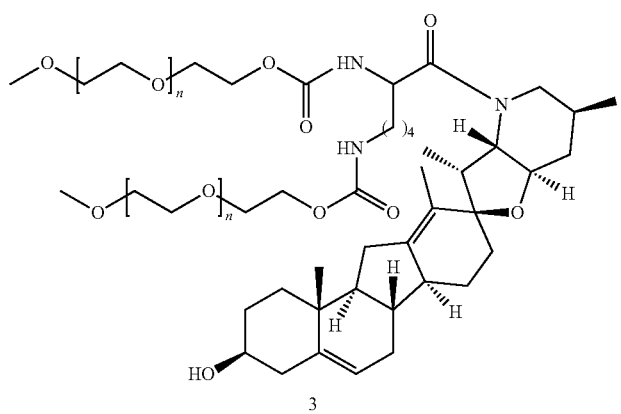

3

A mixture of Y-type-mPEG-NHS-40K (4.0 g, 0.05 mmol) and cyclopamine (22.6 mg, 0.055 mmol, 1.1 equivalent of compound 1) in 20.0 mL of anhydrous dichloromethane was stirred at room temperature for 24 hours. The mixture was evaporated under a reduced pressure to about 5.0 mL, to which were then added 5.0 mL of water and a dialysis bag (MWCO 35000), and thereafter the solution was dialyzed against water (2 L) for 24 hours (changing water 2.0 L×3 times). The solution was then freeze-dried into a solid compound. The solid compound was recrystallized by firstly dissolved in dichloromethane and then precipitated with ethyl ether, and thereafter dried under vacuum and 35° C., to obtain 3.75 g of the final compound (compound 3).

$^{13}C$ NMR (100 MHz, $CD_2Cl_2$) δ 172.31 (linker), 158.62 (PEG), 158.31 (PEG), 142.3 (C-12), 141.9 (C-5), 127.0 (C-13), 121.7 (C-6), 85.1 (C-17), 75.5 (C-23), 71.7 (C-3), 71.13 (PEG), 69.62 (PEG), 65.96 (C-22), 61.73 (C-26), 51.92 (C-9), 49.1 (C-14), 41.9 (2C, C-4 and C-8), 39.9 (C-20), 39.2 (C-24), 38.2 (C-1), 36.5 (C-10), 31.6 (C-16), 31.7 (C-25), 31.5 (C-2), 31.1 (C-7), 28.8 (C-11), 24.7 (C-15), 18.7 (C-27), 18.4 (C-19), 12.6 (C-18), 10.3 (C-21).

EXAMPLE 3

A mixture of 4-armed-mPEG-COOH-10K (1.0 g, 0.05 mmol) and cyclopamine (90.4 mg, 0.22 mmol, 1.1 equivalent of compound 1) in 7.5 mL of anhydrous dichloromethane was stirred at room temperature for 24 hours. The mixture was evaporated under a reduced pressure to about 3.0 mL, to which were then added 5.0 mL of water and a dialysis bag (MWCO 10000), and thereafter the solution was dialyzed against water (2 L) for 24 hours (changing water 2.0 L×3 times). The solution was then freeze-dried into a solid compound. The solid compound was recrystallized by firstly dissolved in dichloromethane and then precipitated with ethyl ether, and thereafter dried under vacuum and 35° C., to obtain 3.75 g of the final compound (compound 4).

$^{13}C$ NMR (100 MHz, $CD_2Cl_2$) δ 174.35 (PEG), 142.2 (C-12), 141.9 (C-5), 127.0 (C-13), 121.7 (C-6), 85.0 (C-17), 75.6 (C-23), 71.7 (C-3), 70.96 (PEG), 69.52 (PEG), 66.33 (C-22), 61.21 (C-26), 52.1 (C-9), 49.1 (C-14), 41.9 (2C, C-4 and C-8), 39.9 (C-20), 39.0 (C-24), 38.2 (C-1), 36.4 (C-10), 31.9 (C-16), 31.7 (C-25), 31.5 (C-2), 31.1 (C-7), 28.8 (C-11), 24.7 (C-15), 18.7 (C-27), 18.4 (C-19), 12.3 (C-18), 10.2 (C-21).

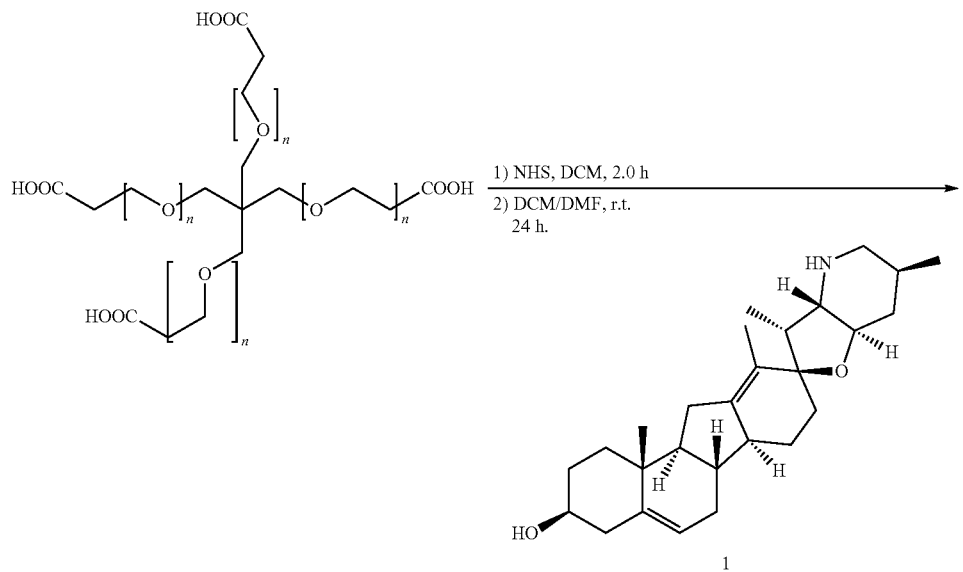

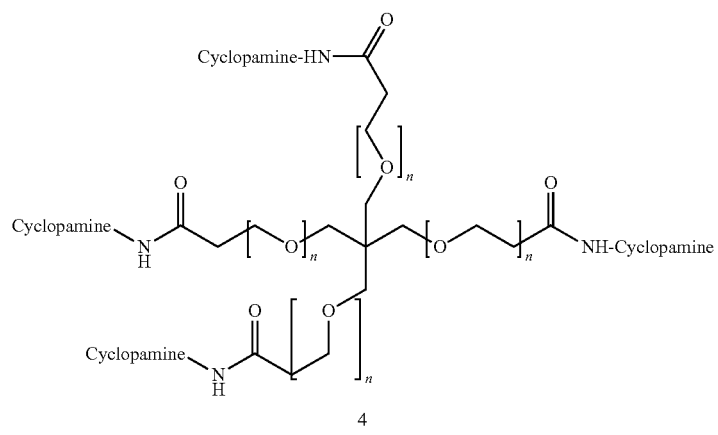

EXAMPLE 4

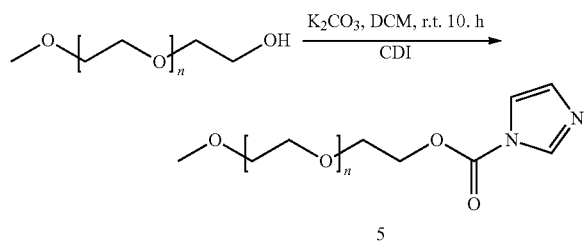

To a mixture of mPEG 5000 (5.0 g, 0.1 mmol) in 20.0 mL of DCM, were added K$_2$CO$_3$ (13.8 mg, 0.1 mmol) and solid CDI (19.45 mg, 0.12 mmol) in additional 20 mL of DCM, followed by stirring overnight (for about 12 hours) at room temperature. The mixture was concentrated to about 5.0 mL, and then dialyzed against water (2.0 L) through a dialysis bag (MWCO 5000) (changing water 2.0 L×3 times). The solution was then freeze-dried into a solid compound. The solid compound was recrystallized by firstly dissolved in dichloromethane and then precipitated with ethyl ether so as to remove decomposed PEG, and thereafter dried under vacuum and 35° C., to obtain 4.97 g of the final compound (compound 5).

$^1$H NMR (400 MHz, CDCl$_3$): 8.12 (s), 7.40 (s), 4.22 (m), 3.65-3.53 (broad peak).

EXAMPLE 5

A mixture of CDI-mPEG (1.0 g, about 0.2 mmol) and cyclopamine (90.4 mg, 0.22 mmol, 1.1 equivalent of compound 1) in 7.5 mL of anhydrous dichloromethane was stirred at room temperature for 24 hours. The mixture was evaporated under a reduced pressure to about 3.0 mL, to which were then added 5.0 mL of water and a dialysis bag (MWCO 5000), and thereafter the solution was dialyzed against water (2 L) for 24 hours (changing water 2.0 L×3 times). The solution was then freeze-dried into a solid compound. The solid compound was recrystallized by firstly dissolved in dichloromethane and then precipitated with ethyl ether, and thereafter dried under vacuum and 35° C., to obtain 0.83 g of the final compound (compound 6).

$^{13}$C NMR (100 MHz, CD$_2$Cl$_2$) δ 157.32 (PEG), 141.8 (C-12), 141.9 (C-5), 127.2 (C-13), 121.7 (C-6), 85.0 (C-17), 75.6 (C-23), 71.7 (C-3), 71.2 (PEG), 69.32 (PEG), 66.33 (C-22), 61.21 (C-26), 52.1 (C-9), 49.1 (C-14), 41.9 (C-4 and C-8), 39.9 (C-20), 39.0 (C-24), 38.2 (C-1), 36.4 (C-10), 31.9 (C-16), 31.7 (C-25), 31.5 (C-2), 31.1 (C-7), 28.7 (C-11), 24.7 (C-15), 18.7 (C-27), 18.5 (C-19), 12.3 (C-18), 10.3 (C-21).

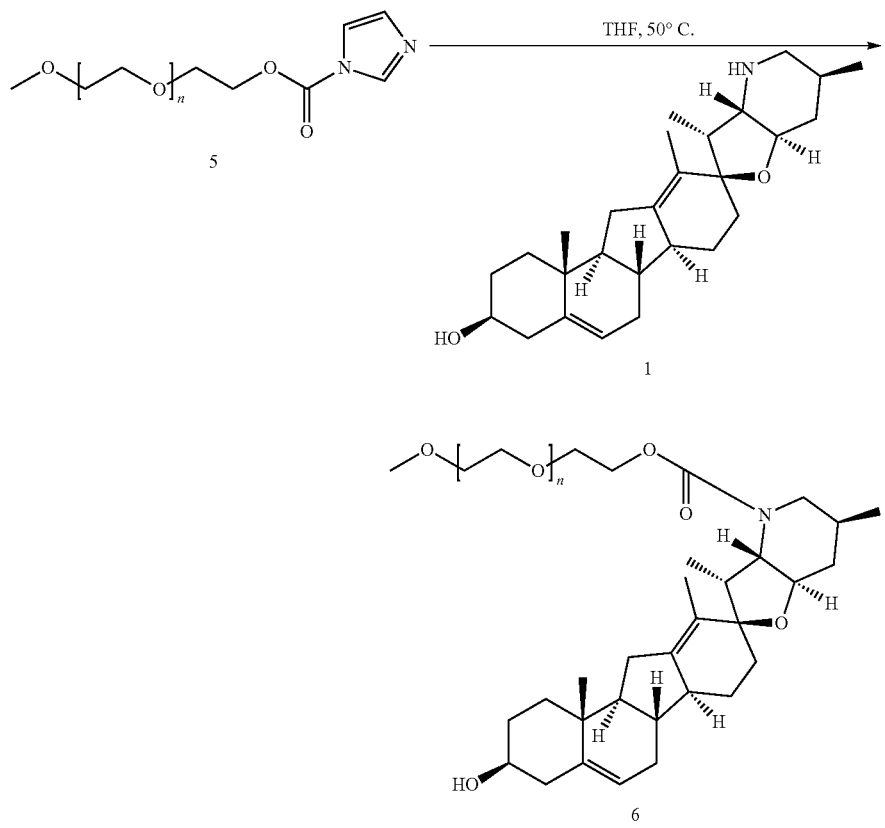

EXAMPLE 6

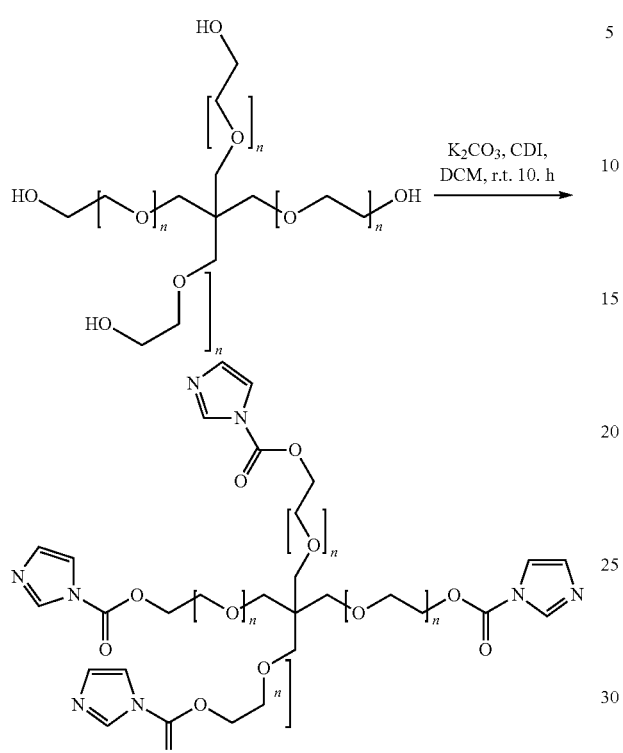

To a mixture of 4-armed-PEG 10K (5.0 g, 0.5 mmol) in 20.0 mL of DCM, were added $K_2CO_3$ (276 mg, 2.0 mmol) and solid CDI (392 mg, 2.40 mmol) in additional 20 mL of DCM, followed by stirring overnight (for about 12 hours) at room temperature. The mixture was concentrated to about 5.0 mL, and then dialyzed against water (2.0 L) through a dialysis bag (MWCO 10000) (changing water 2.0 L×3 times). The solution was then freeze-dried into a solid compound. The solid compound was recrystallized by firstly dissolved in dichloromethane and then precipitated with ethyl ether so as to remove decomposed PEG, and thereafter dried under vacuum and 35° C., to obtain 5.02 g of the final compound (compound 7).

$^1$H NMR (400 MHz, $CDCl_3$): 8.15 (m), 7.38 (m), 4.21 (m), 3.66-3.47 (broad peak).

EXAMPLE 7

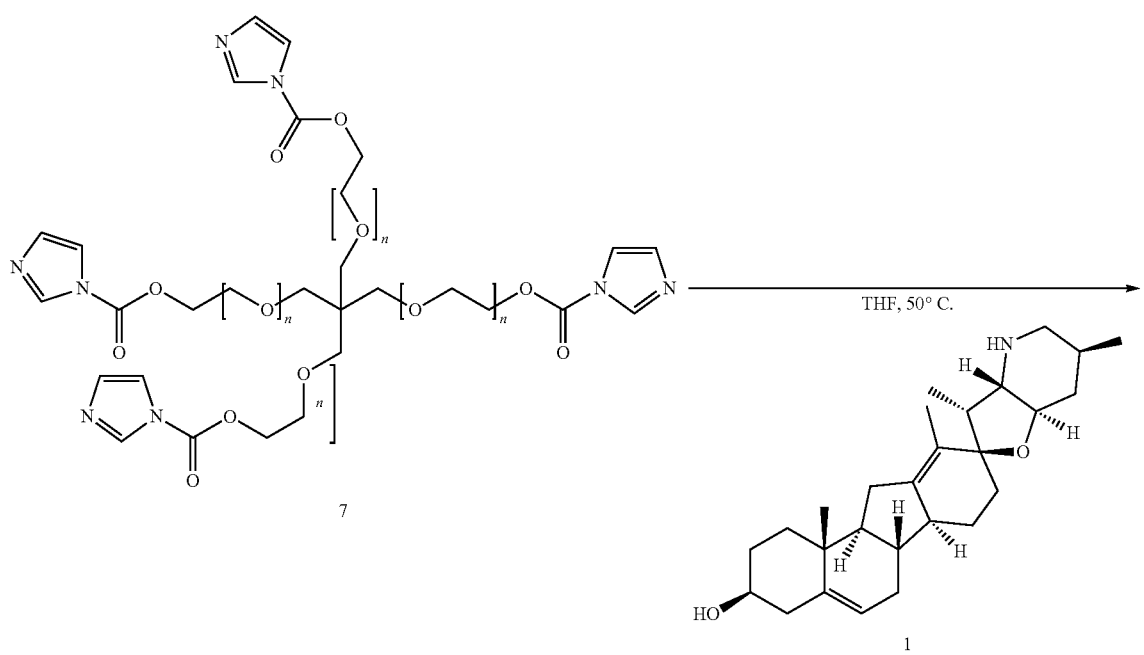

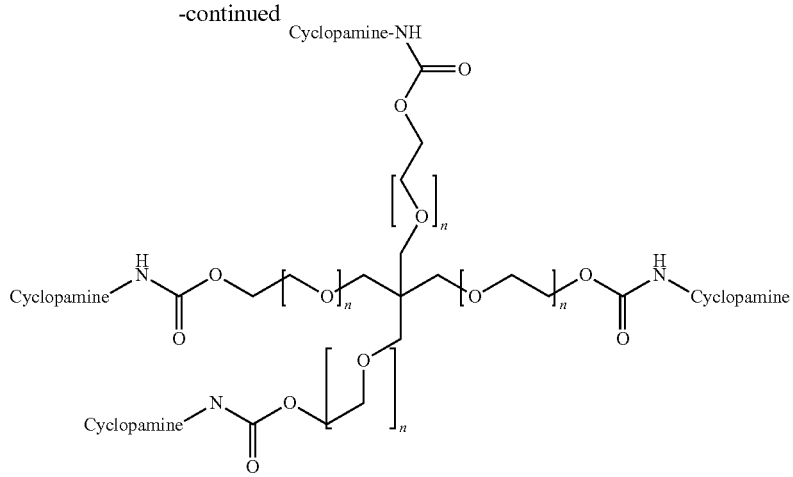

A mixture of a-armed-CDI-mPEG-10K (1.0 g, about 0.1 mmol) and cyclopamine (181 mg, 0.44 mmol, 1.1 equivalent of compound 1) in 7.5 mL of anhydrous dichloromethane was stirred at room temperature for 24 hours. The mixture was evaporated under a reduced pressure to about 3.0 mL, to which were then added 5.0 mL of water and a dialysis bag (MWCO 10000), and thereafter the solution was dialyzed against water (2 L) for 24 hours (changing water 2.0 L×3 times). The solution was then freeze-dried into a solid compound. The solid compound was recrystallized by firstly dissolved in dichloromethane and then precipitated with ethyl ether, and thereafter dried under vacuum and 35° C., to obtain 0.95 g of the final compound (compound 8).

$^{13}C$ NMR (100 MHz, $CD_2Cl_2$) δ 157.32 (PEG), 142.3 (C-12), 141.9 (C-5), 127.2 (C-13), 121.7 (C-6), 85.0 (C-17), 75.6 (C-23), 71.7 (C-3), 70.9 (PEG), 69.25 (PEG), 66.33 (C-22), 61.21 (C-26), 52.1 (C-9), 49.1 (C-14), 41.9 (C-4 and C-8), 39.9 (C-20), 39.0 (C-24), 38.2 (C-1), 36.4 (C-10), 31.9 (C-16), 31.7 (C-25), 31.5 (C-2), 31.1 (C-7), 28.7 (C-11), 24.7 (C-15), 18.7 (C-27), 18.5 (C-19), 12.3 (C-18), 10.4 (C-21).

EXAMPLE 8

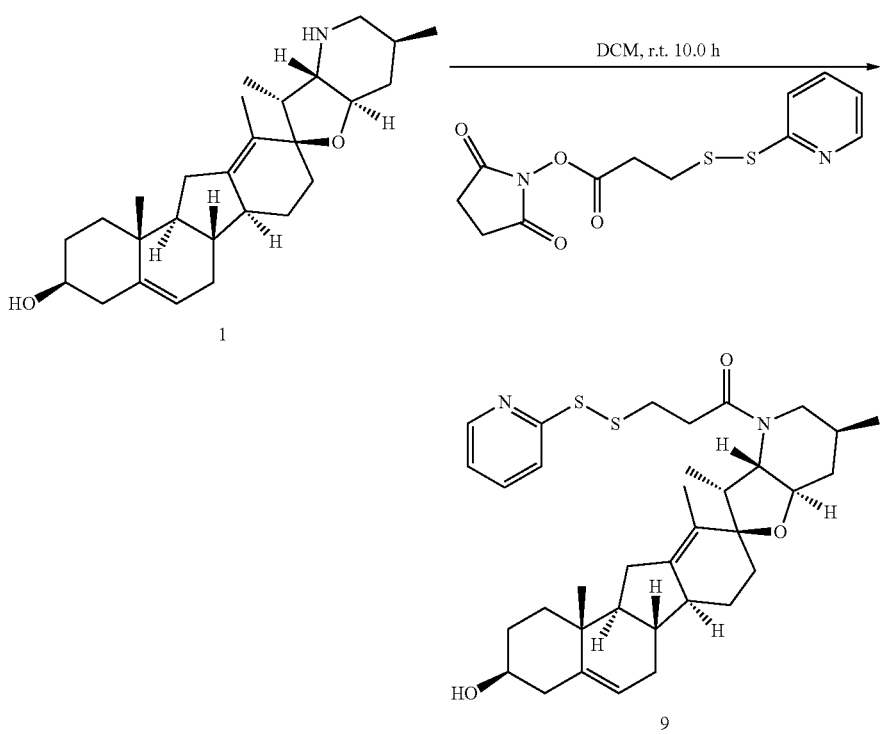

A mixture of cyclopamine (1) (1.027 g, 2.5 mmol) and N-succimide 3-(2-pyridyldithio)propionate (SPDP) (1.170 g, 1.5 eq, 3.75 mmol) in 15 mL of anhydrous dichloromethane (DCM) was stirred at room temperature for 10 hours, washed with sodium bicarbonate and brine, concentrated under vacuum and purified by preparative HPLC to give 1.25 g of a white solid (82%, purity >98%) (compound 9).

$^1$H NMR (400 MHz, CD$_2$Cl$_2$) 8.78 (d, 1H), 7.86 (dd, 2H), 7.28 (d, 1H), 5.42 (m, 1H,), 3.50 (m, 1H), 3.18 (dd, 1H), 3.03 (dd, 1H), 2.96 (d, 2H), 2.64-2.62 (b, 3H), 2.41 (m, 1H); 2.37 (dd, 1H), 2.27 (m, 3H), 2.23 (m, 1H), 2.18 (m, 1H), 2.11 (m, 1H), 1.89 (m, 1H), 1.82 (m, 2H), 1.78 (m, 2H), 1.71 (m, 1H), 1.65 (s, 3H), 1.57 (m, 2H), 1.51 (m, 1H), 1.44 (m, 1H), 1.30 (m, 1H), 1.25 (m, 1H), 1.23 (m, 1H), 1.15 (m, 1H), 1.01 (s, 3H), 0.94 (dd, 3H), 0.92 (d, 3H);

LC-MS (m/z): C$_{35}$H$_{48}$N$_2$O$_3$S$_2$, [M+H]+: 609.42.

EXAMPLE 9

At 0° C., to the solution of compound (9) (1.0 g, 1.6 mmol) in 5.0 mL of anhydrous dichloromethane, was added 2-aminoethanethiol (0.25 g, 2.0 eq, 3.2 mmol) in 2.0 mL of anhydrous dichloromethane. The resulting solution was stirred at room temperature for 6 hours, washed with sodium bicarbonate and brine, concentrated under vacuum, purified by preparative HPLC, and dried under vacuum and 35° C. to give 0.616 g of the final compound (67%, purity >98%) (compound 10).

$^1$H NMR (400 MHz, CD$_2$Cl$_2$) 5.61-5.38 (b, around 3H,), 3.67 (m, 2H), 3.50 (m, 1H), 3.18 (dd, 1H), 3.05-2.97 (m, 5H), 2.64-2.62 (b, 3H), 2.41 (m, 1H); 2.37 (dd, 1H), 2.27 (m, 3H), 2.23 (m, 1H), 2.18 (m, 1H), 2.11 (m, 1H), 1.89 (m, 1H), 1.83 (m, 1H), 1.81 (m, 1H), 1.78 (m, 1H), 1.76 (m, 1H), 1.72 (m, 1H), 1.64 (s, 3H), 1.58 (m, 1H), 1.55 (m, 1H), 1.51 (m, 1H), 1.44 (m, 1H), 1.31 (m, 1H), 1.25 (m, 1H), 1.23 (m, 1H), 1.13 (m, 1H), 1.00 (s, 3H), 0.93 (dd, 6H);

$^{13}$C NMR (100 MHz, CD$_2$Cl$_2$) δ 142.2 (C-12), 141.9 (C-5), 127.0 (C-13), 121.7 (C-6), 85.0 (C-17), 75.6 (C-23), 71.7 (C-3), 66.5 (C-22), 54.9 (C-26), 52.1 (C-9), 49.1 (C-14), 41.9 (2C, C-4 and C-8), 39.9 (C-20), 39.2 (C-24), 38.2 (C-1), 36.5 (C-10), 31.9 (C-16), 31.7 (C-25), 31.5 (C-2), 31.1 (C-7), 28.8 (C-11), 24.7 (C-15), 18.7 (C-27), 18.4 (C-19), 12.8 (C-18), 10.4 (C-21);

LC-MS (m/z): C$_{32}$H$_{50}$N$_3$O$_3$S$_2$, [M+H]+: 575.51.

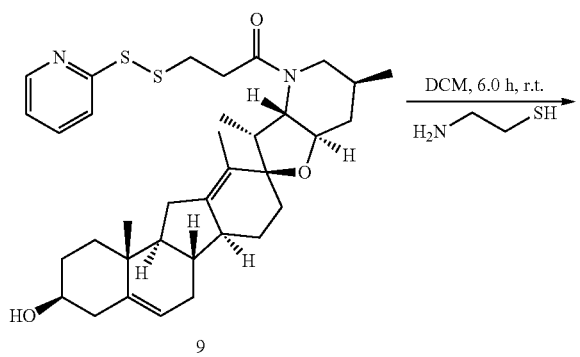

EXAMPLE 10

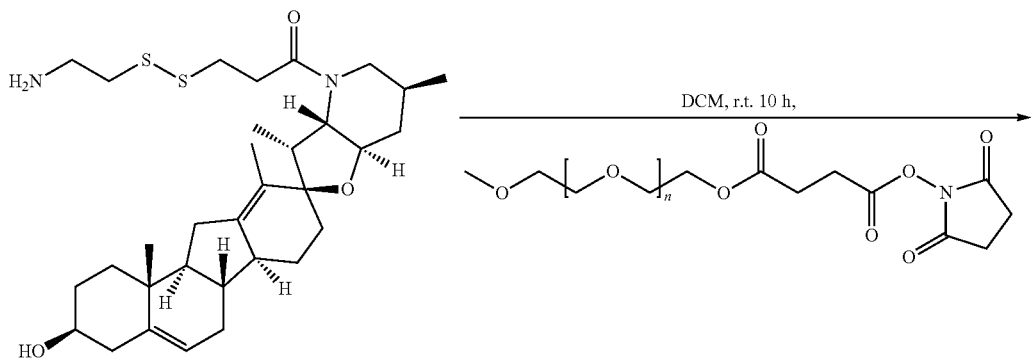

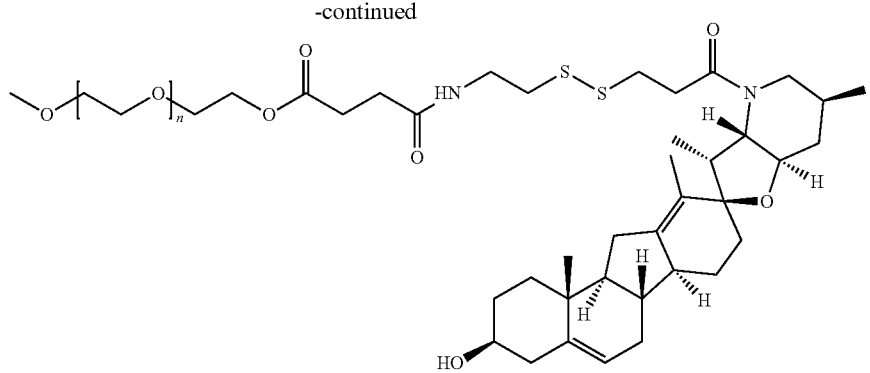

A mixture of mPEG-NHS-20K (1.0 g, 0.05 mmol) and compound 10 (31.6 mg, 0.055 mmol, 1.1 equivalent) in 10.0 mL of anhydrous dichloromethane was stirred at room temperature for 24 hours. The mixture was evaporated under a reduced pressure to about 1.5 mL, to which were then added 5.0 mL of water and a dialysis bag (MWCO 20000), and thereafter the solution was dialyzed against water (2 L) for 24 hours (changing water 2.0 L×3 times). The solution was then freeze-dried into a solid compound. The solid compound was recrystallized by firstly dissolved in dichloromethane and then precipitated with ethyl ether, and thereafter dried under vacuum and 35° C., to obtain 0.863 g of the final compound (compound 11).

$^{13}$C NMR (100 MHz, CD$_2$Cl$_2$) δ 175.2, 174.82, 172.31 (PEG), 142.2 (C-12), 141.9 (C-5), 127.0 (C-13), 121.7 (C-6), 85.0 (C-17), 75.6 (C-23), 71.7 (C-3), 71.26 (PEG), 69.63 (PEG), 67.3 (C—O, PEG), 66.30 (C-22), 61.54 (C-26), 55.7 (C—N), 52.1 (C-9), 49.1 (C-14), 41.9 (C-4 and C-8), 40.5 (S—C), 39.9 (C-20), 39.0 (C-24), 38.2 (C-1), 36.7 (C-10), 33.6 (linker C), 32.1 (C-16), 31.8 (C-25), 31.3 (C-2), 31.1 (C-7), 28.8 (C-11), 24.7 (C-15), 18.7 (C-27), 18.3 (C-19), 12.7 (C-18), 10.3 (C-21).

EXAMPLE 11

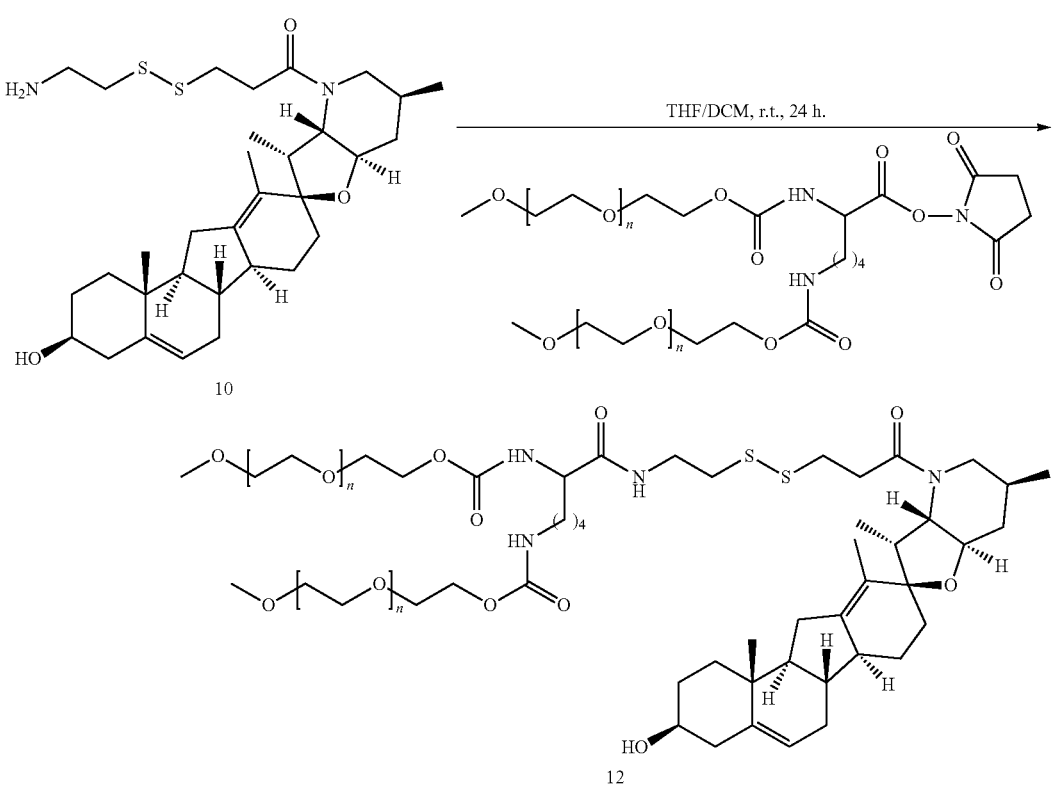

A mixture of Y-type-mPEG-NHS-40K (4.0 g, 0.05 mmol) and compound 10 (31.6 mg, 0.055 mmol, 1.1 equivalent of compound 1) in 20.0 mL of anhydrous dichloromethane and anhydrous THF (3:2) was stirred at room temperature for 24 hours. The mixture was evaporated under a reduced pressure to about 5.0 mL, to which were then added 5.0 mL of water and a dialysis bag (MWCO 35000), and thereafter the solution was dialyzed against water (2 L) for 24 hours (changing water 2.0 L×3 times). The solution was then freeze-dried into a solid compound. The solid compound was recrystallized by firstly dissolved in dichloromethane and then precipitated with ethyl ether, and thereafter dried under vacuum and 35° C., to obtain 3.85 g of the final compound (compound 12).

$^{13}$C NMR (100 MHz, CD$_2$Cl$_2$) δ 175.1, 174.76, 172.42 (PEG), 142.2 (C-12), 141.9 (C-5), 127.0 (C-13), 121.7 (C-6), 85.0 (C-17), 75.6 (C-23), 71.7 (C-3), 71.26 (PEG), 69.63 (PEG), 66.94 (C—O, PEG), 66.30 (C-22), 61.54 (C-26), 55.7 (C—N), 52.1 (C-9), 49.1 (C-14), 42.1 (C-4 and C-8), 40.6 (S—C), 39.9 (C-20), 39.2 (C-24), 38.2 (C-1), 36.7 (C-10), 33.5 (linker C), 32.1 (C-16), 31.6 (C-25), 31.4 (C-2), 31.01 (C-7), 28.7 (C-11), 24.4 (C-15), 19.0 (C-27), 18.4 (C-19), 12.6 (C-18), 10.3 (C-21).

EXAMPLE 12

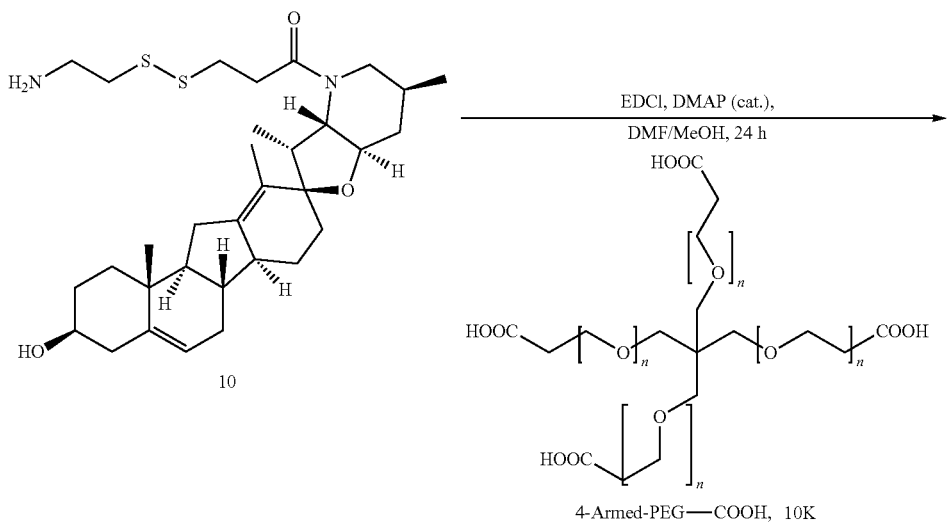

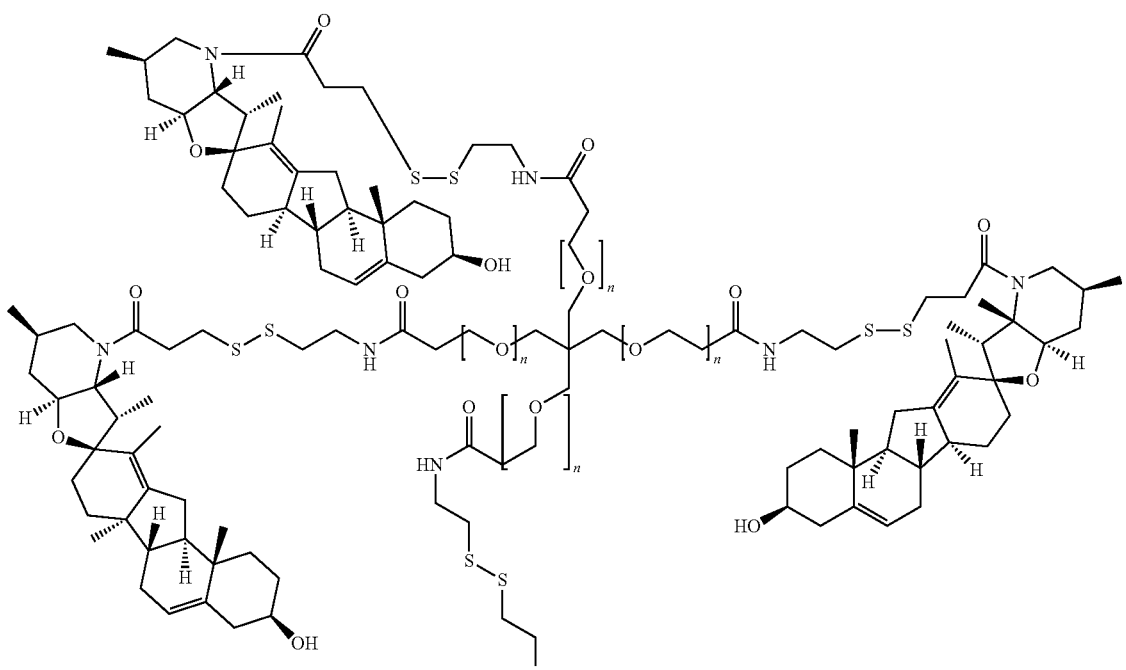

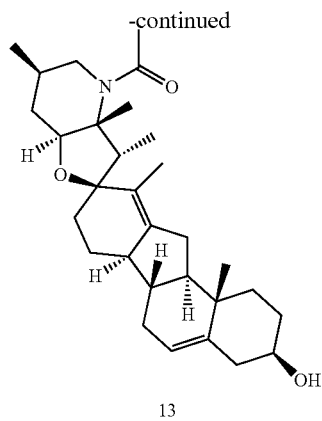

13

A mixture of 4-armed-mPEG-COOH-10K (1.0 g, 0.05 mmol), 1.0 eq of EDCI, 0.2 eq of DMAP and compound 10 (126.3 mg, 0.22 mmol, 1.1 equivalent) in 7.5 mL of anhydrous DMF and THF (2:1) was stirred at room temperature for 24 hours. The mixture was evaporated under a reduced pressure to about 5.0 mL, to which were then added 5.0 mL of water and a dialysis bag (MWCO 10000), and thereafter the solution was dialyzed against water (2 L) for 24 hours (changing water 2.0 L×3 times). The solution was then freeze-dried into a solid compound. The solid compound was recrystallized by firstly dissolved in dichloromethane and then precipitated with ethyl ether, and thereafter dried under vacuum and 35° C., to obtain 1.02 g of the final compound (compound 13).

$^{13}$C NMR (100 MHz, CD$_2$Cl$_2$) δ 174.54 (PEG), 174.27 (PEG), 141.9 (C-12), 141.7 (C-5), 127.0 (C-13), 121.7 (C-6), 85.0 (C-17), 75.6 (C-23), 71.7 (C-3), 71.33 (PEG), 71.25 (PEG), 69.71 (PEG), 69.53 (PEG), 67.10 (C—O, PEG), 66.30 (C-22), 61.54 (C-26), 55.7 (C—N), 52.1 (C-9), 49.1 (C-14), 42.1 (C-4 and C-8), 40.81 (S—C), 40.5 (S—C), 39.9 (C-20), 39.2 (C-24), 38.2 (C-1), 36.7 (C-10), 33.8-33.6 (linker C), 32.1 (C-16), 31.6 (C-25), 31.4 (C-2), 31.01 (C-7), 28.7 (C-11), 24.4 (C-15), 19.0 (C-27), 18.4 (C-19), 12.6 (C-18), 10.2 (C-21).

EXAMPLE 13

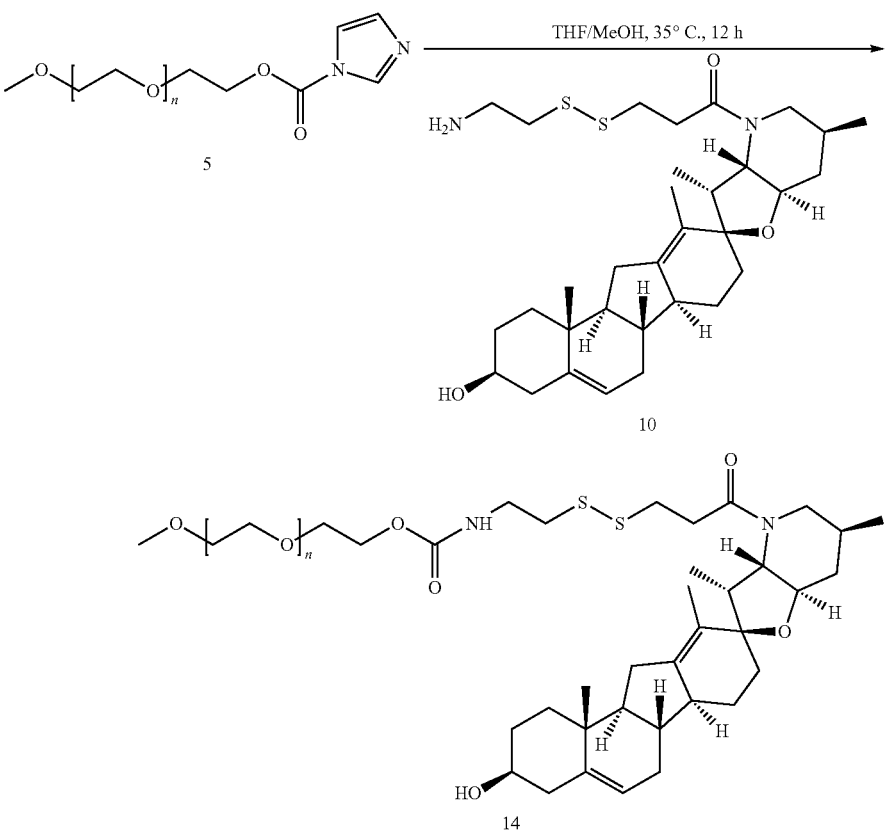

A mixture of CDI-mPEG (1.0 g, about 0.2 mmol, compound 5) and compound 10 (126.3 mg, 0.22 mmol, 1.1 equivalent of compound 1) in 7.5 mL of anhydrous THF/MeOH (12:1) was stirred at 35° C. for 12 hours. The mixture was evaporated under a reduced pressure to about 3.0 mL, to which were then added 5.0 mL of water and a dialysis bag (MWCO 5000), and thereafter the solution was dialyzed against water (2 L) for 24 hours (changing water 2.0 L×3 times). The solution was then freeze-dried into a solid compound. The solid compound was recrystallized by firstly dissolved in dichloromethane and then precipitated with ethyl ether, and thereafter dried under vacuum and 35° C., to obtain 0.92 g of the final compound (compound 14).

$^{13}$C NMR (100 MHz, CD$_2$Cl$_2$): δ 174.6 (linker), 157.32 (PEG), 141.8 (C-12), 141.9 (C-5), 127.2 (C-13), 121.7 (C-6), 85.0 (C-17), 75.6 (C-23), 71.7 (C-3), 71.3 (PEG), 69.5 (PEG), 66.8, 66.33 (C-22), 61.21 (C-26), 52.1 (C-9), 49.1 (C-14), 41.9 (C-4 and C-8), 40.7 (C—S), 39.8 (C20), 39.0 (C-24), 38.2 (C-1), 36.4 (C-10), 33.8, 31.9 (C-16), 31.7 (C-25), 31.5 (C-2), 31.1 (C-7), 28.7 (C-11), 24.7 (C-15), 18.7 (C-27), 18.5 (C-19), 12.3 (C-18), 10.3 (C-21).

EXAMPLE 14

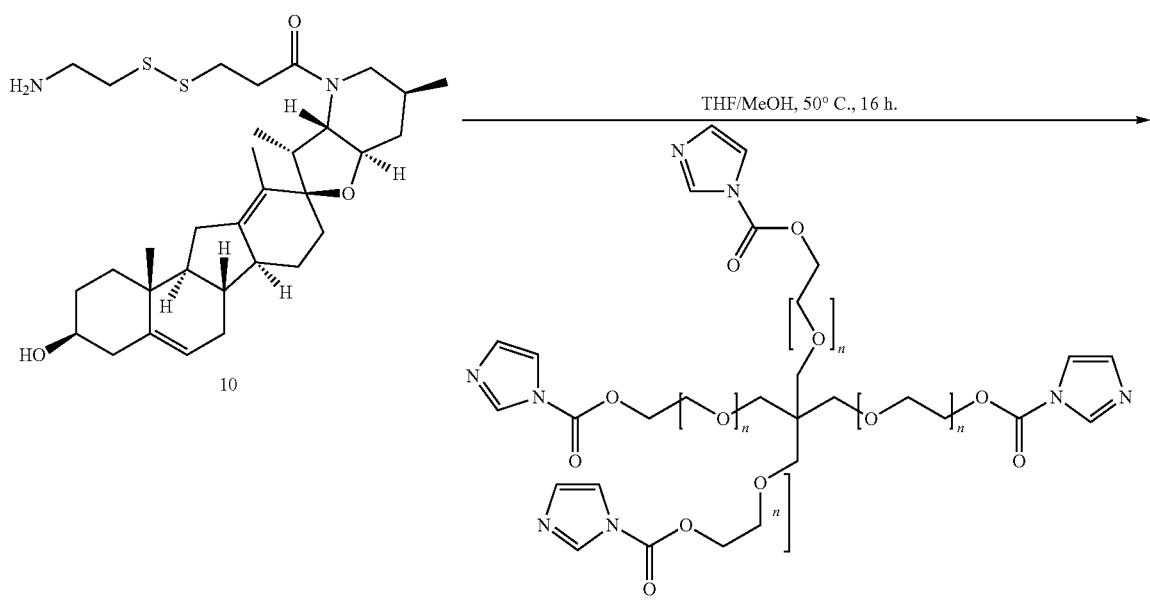

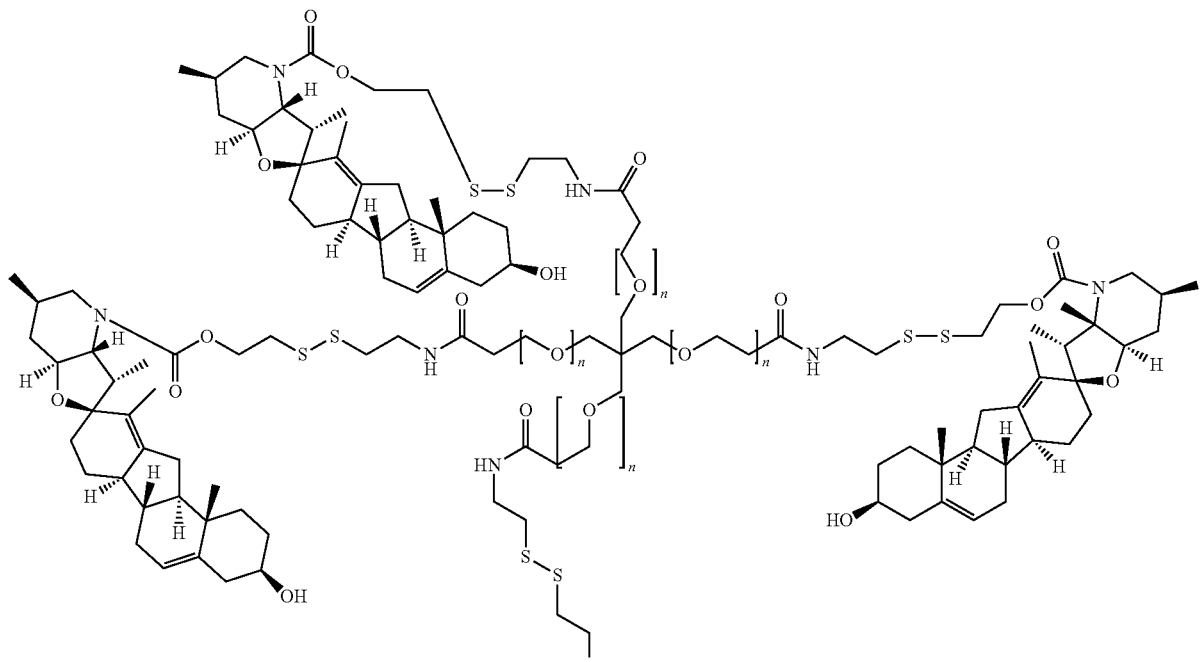

-continued

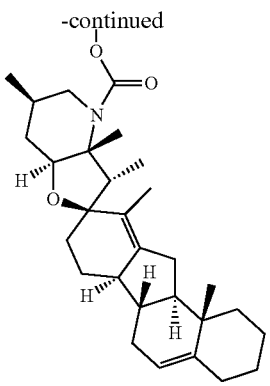

15

A mixture of a-armed-CDI-mPEG-10K (1.0 g, about 0.1 mmol, compound 7) and compound 10 (252.6 mg, 0.44 mmol, 1.1 equivalent) in 7.5 mL of anhydrous THF/MeOH (2:1) was stirred at 50° C. for 16 hours. The mixture was evaporated under a reduced pressure to about 3.0 mL, to which were then added 5.0 mL of water and a dialysis bag (MWCO 10000), and thereafter the solution was dialyzed against water (2 L) for 24 hours (changing water 2.0 L×3 times). The solution was then freeze-dried into a solid compound. The solid compound was recrystallized by firstly dissolved in dichloromethane and then precipitated with ethyl ether, and thereafter dried under vacuum and 35° C., to obtain 1.12 g of the final compound (compound 15).

$^{13}$C NMR (100 MHz, CD$_2$Cl$_2$) δ 174.7, 174.5, 173.9, 157.56 and 157.32 (PEG), 142.5 (C-12), 141.8 (C-5), 127.1 (C-13), 121.8 (C-6), 85.2 (C-17), 75.6 (C-23), 71.8 (C-3), 71.2 (PEG), 69.3 (PEG), 66.7, (PEG), 66.33 (C-22), 61.21 (C-26), 52.1 (C-9), 49.1 (C-14), 41.8 (C-4 and C-8), 40.84 and 40.52 (S—C), 40.1 (C-20), 39.0 (C-24), 38.2 (C-1), 36.4 (C-10), 31.9 (C-16), 31.7 (C-25), 31.5 (C-2), 31.1 (C-7), 28.7 (C-11), 24.7 (C-15), 18.7 (C-27), 18.5 (C-19), 12.3 (C-18), 10.4 (C-21).

Biological Activity Assay:
Study of Stability in Plasma

The corresponding PEG-cyclopamine (25.0 mg) and plasma (Biomeda, Calif.) 150 µL were incubated at 37° C. for different periods, i.e., 0, 2, 4, 6, 20, 24, 36, 48, 72 and 144 hours. The mixture was quenched with a CH$_3$CN/MeOH mixture (800 µL) in a ratio of 1:1, swirled for 1 minute, and then filtered through a 0.2 µm filter membrane. 30 µl of the resulting filtrate was analyzed by HPLC, to measure the disappearance of the conjugate. The results were as shown in Table 1 below.

TABLE 1

The experimental results on stability in plasma of the compounds of the present invention

| Serial No. of compound | disappearance % | | | | | | | |
|---|---|---|---|---|---|---|---|---|
| | 2 h | 4 h | 6 h | 24 h | 36 h | 48 h | 72 h | 144 h |
| cyclopamine | 32 | 68 | | 83 | | | | |
| compound 2 | 0 | 0 | 0 | 14 | 20 | 20 | 26 | 38 |
| compound 6 | 0 | 0 | 0 | 9 | 11 | 15 | 19 | 26 |
| compound 8 | 0 | 0 | 0 | 8 | 10 | 15 | 18 | 20 |
| compound 12 | 0 | 0 | 0 | 7 | 10 | 16 | 19 | 28 |
| compound 15 | 0 | 0 | 0 | 11 | 15 | 21 | 30 | 41 |

As can be seen from Table 1, the compounds of the present invention had good stability in plasma.

Study of pH Stability

Figure 2:
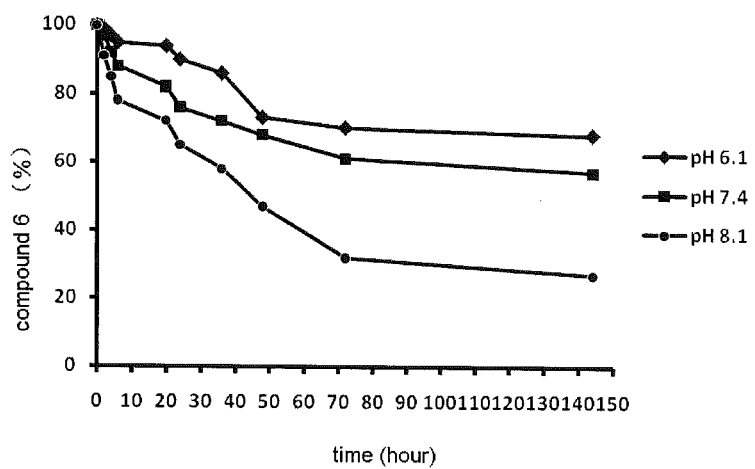
FIG. 2: A graph of the residual amount (expressed in percentage) of compound 6 at different pH values (6.1, 7.3 and 8.1) along with time (0, 2, 4, 6, 20, 24, 36, 48, 72 and 144 h).
Figure 3:
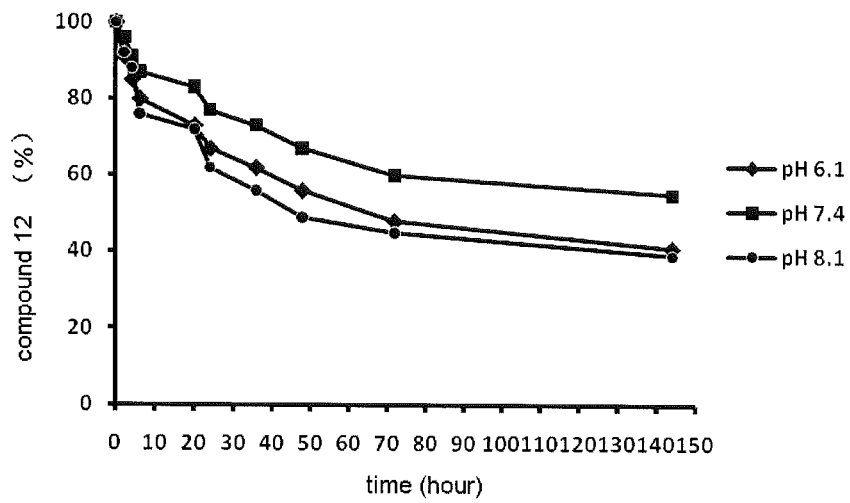
FIG. 3: A graph of the residual amount (expressed in percentage) of compound 12 at different pH values (6.1, 7.3 and 8.1) along with time (0, 2, 4, 6, 20, 24, 36, 48, 72 and 144 h).

The corresponding PEG-cyclopamine compounds (Compounds 2, 6, 12) (10 mg/ml) were diluted in phosphate buffer salines at different pH values (6.1, 7.4, 8.1) respectively, and incubated at 37° C. Aliquots were taken at different time points, to which was added an equal volume of DMSO, and then analyzed by HPLC to determine the disappearance of the conjugate. By plotting the percentages of the remaining starting compound versus time, a stability characteristic graph was obtained. The percentages were calculated according to the ratios of the peak areas of the sample at 0, 2, 4, 6, 20, 24, 36, 48, 72 and 144 hours to the starting peak area. Each stability characteristic diagram represented the average values of two independent operations according to the same sampling schedule. The standard deviation for each point was generally 2% or lower. The results were shown in FIG. 1-3. The results showed that the compounds of the present invention had good stability at a pH value in the range of 6.1-8.1.

Cytotoxicity In Vitro

All cell lines were obtained from the American Type Culture Collection, and grown in the following media: COLO 205 and OVCAR-3 (RPMI 1640, containing 4.5 g/L glucose, 10 mM HEPES, 1 mM sodium pyruvate, 10% FBS); HT-29 (McCoy's 5a, containing 1.5 mM L-glutamine, 10% FBS); A549 (Ham's F12K, containing 10% FBS). All cell lines were maintained in an incubator at 37° C. containing 5% CO$_2$. The cytotoxicity in vitro of the corresponding PEG-cyclopamine and CT-11 was measured by using cell proliferation tetrazolium dye analytic method (MTS analytic method). Briefly, the day before the start of the experiment the cells were incubated in a 96-well plate in a quantity of 10,000-20,000/well. The cells were treated with a series of dilutions of the corresponding PEG-cyclopamine, CPT-11 or cyclopamine dissolved in DMSO, and then incubated in an incubator at 37° C. for 3-4 days. At the end of the incubation period, an MTS dye was added, and then the colored product formazane as formed was measured by a Spectramax 340PC reader (Molecular Devices, CA) at 490 nm. (IC50: µM)

A interval was less than 0.100 µM; B interval was greater than 0.100 µM but less than 0.500 µM; C interval was greater than 0.500 µM but less than 2.000 µM; D interval was greater than 2.000 µM.

TABLE 2

Experimental results of cytotoxicity in vitro

| Serial No. of compound | COLO205 | HT 29 | OVCAR3 | A549 |
|---|---|---|---|---|
| cyclopamine | B | B | B | D |
| compound 2 | B | B | A | C |
| compound 4 | B | B | A | D |
| compound 8 | A | C | B | D |
| compound 12 | A | B | A | C |
| compound 15 | A | B | A | D |

Figure 4:
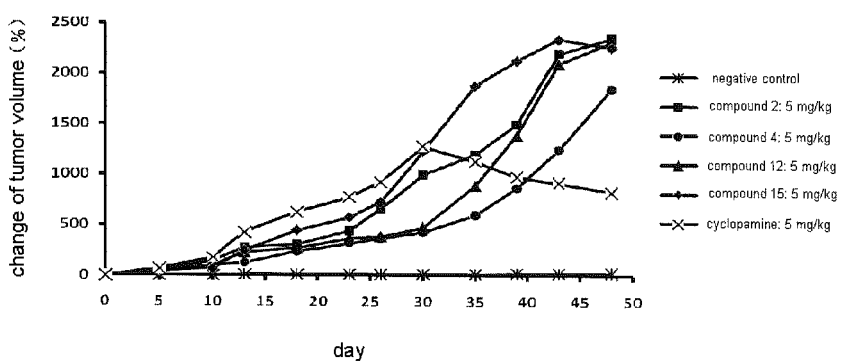
FIG. 4: A graph exhibiting the influences of compounds 2, 4, 12, 15, and cyclopamine on the volume of tumor.

Study of Efficacy In Vivo:

Human breast carcinoma (MX-1) tumor fragments were obtained from DTP, DCTD tumor preservation center, NCI, Bethesda, Md. Subcutaneous (s.c.) tumor xenograft model was established (4-5 weeks) in right axillary flank of female nude mice by injection of human cancer cells or tumor fragments. MX-1 tumor model was established by implanting 4- to 5-mm³ tissue fragments of MX-1 tumor collected from donor mice in the axillary flank of receptor nude mice. The tests in vivo were carried out by using compounds 2, 4, 12 and 15 with cyclopamine as the control, all of which being administered at a dose of 5 mg/kg, once a day, and three bottles per group. The results were shown in FIG. 4. The results showed that the compounds of the present invention could significantly reduce the volume of tumor. In the above biological activity assay, the PEGylated cyclopamine analogs of the present invention, for example, the PEGylated cyclopamine analogs provided in the examples, had excellent satisfactory results.

The above examples are provided in order to fully disclose and describe how to implement and use the claimed embodiment, rather than to limit the scope disclosed in the present invention. Any modification that is obvious to a person skilled in the art is within the scope of the appended claims. All publications, patents and patent applications cited in the present specification are incorporated herein by reference, as these publications, patents and patent applications are each specially and individually incorporated herein by reference.

The invention claimed is:

1. A PEGylated cyclopamine analog comprising a compound represented by the following formula I:

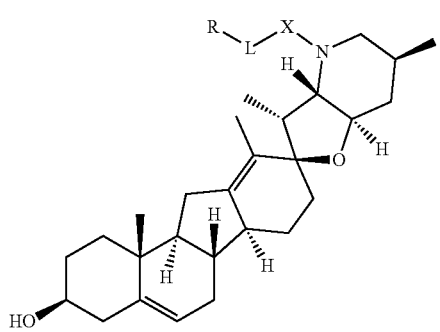

(I)

or a single enantiomer thereof, a mixture of enantiomers, or a mixture of diastereomers, or a pharmaceutically acceptable salt thereof, wherein:

R is straight or branched polyethylene glycol having a molecular weight of 200 to 200,000 Dalton, L is a linking group represented by the following formula II:

(II)

wherein $R_2$ is selected from the group consisting of —NR$^e$C(O)R$^h$ and —NR$^e$C(O)OR$^f$, wherein R$^e$ is each independently selected from the group consisting of hydrogen, $C_{1-6}$ alkyl and $C_{2-6}$ alkenyl, R$^f$ and R$^h$ are each independently selected from the group consisting of $C_{1-6}$ alkylene and $C_{2-6}$ alkenylene;

Y is selected from the group consisting of O, N, S—S, methylene, and ethylidene;

m is an integer of 0-6;

X is a linking group between cyclopamine and L, which is selected from the group consisting of —C(O), —OC(O), —NHC(O), —OS(O)$_2$ and —OS(O).

2. The PEGylated cyclopamine analog according to claim 1, wherein the polyethylene glycol as represented by R has a molecular weight of 300 to 180,000 Dalton, 400 to 160,000 Dalton, 500 to 150,000 Dalton, 600 to 120,000 Dalton, 800 to 100,000 Dalton, 1,000 to 80,000 Dalton, 1,500 to 60,000 Dalton, 2,000 to 50,000 Dalton, 5,000 to 50,000 Dalton, 7,500 to 50,000 Dalton, or 10,000 to 50,000 Dalton.

3. The PEGylated cyclopamine analog according to claim 1, wherein the polyethylene glycol as represented by R is polyethylene glycol represented by the following formula III:

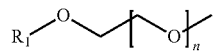

(III)

wherein:

$R_1$ is a terminating group selected from the group consisting of H and $C_{1-12}$ alkyl;

n at each occurrence is independently an integer of 100 to 4500.

4. The PEGylated cyclopamine analog according to claim 1, which is characterized by the following items (1)-(3):

(1) R is straight or branched polyethylene glycol having a molecular weight of 300 to 180,000 Dalton, (2) L is a linking group represented by the following formula II:

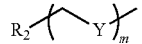

(II)

wherein, $R_2$ is selected from the group consisting of —NR$^e$C(O)R$^h$ and —NR$^e$C(O)OR$^f$, wherein R$^e$ is each independently selected from the group consisting of hydrogen, $C_{1-6}$ alkyl and $C_{2-6}$ alkenyl, R$^f$ and R$^h$ are each independently selected from the group consisting of $C_{1-6}$ alkylene and $C_{2-6}$ alkenylene;

Y is selected from the group consisting of O, N, S—S, methylene and ethylidene;

m is an integer of 0-6;

(3) X is a linking group between cyclopamine and L, which is selected from the group consisting of —C(O), —OC(O), —NHC(O), —OS(O)$_2$ and —OS(O).

5. A PEGylated cyclopamine analog selected from the group consisting of:
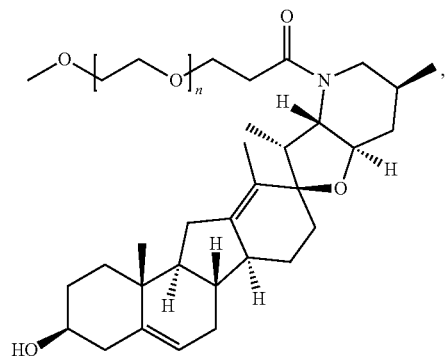
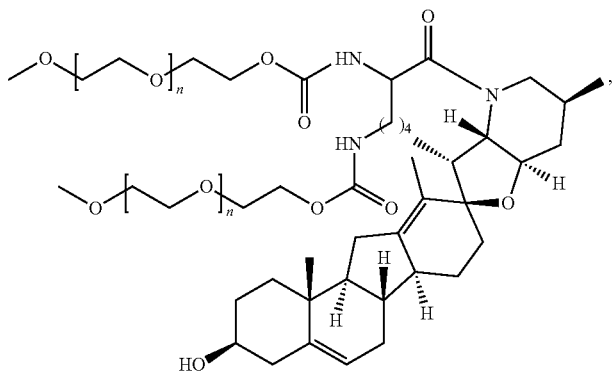
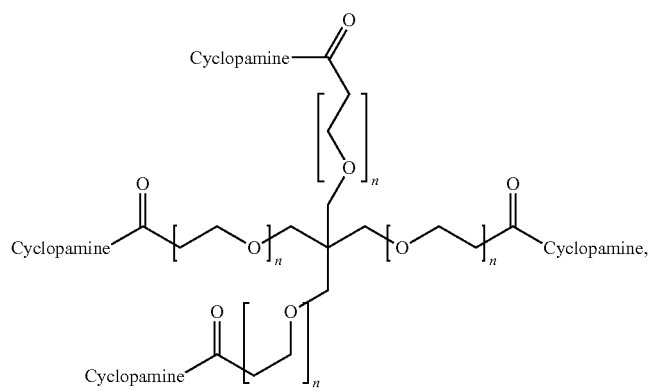
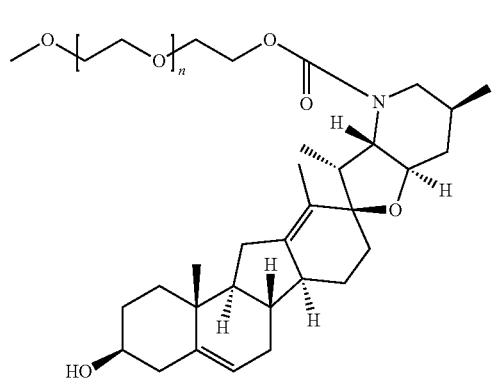
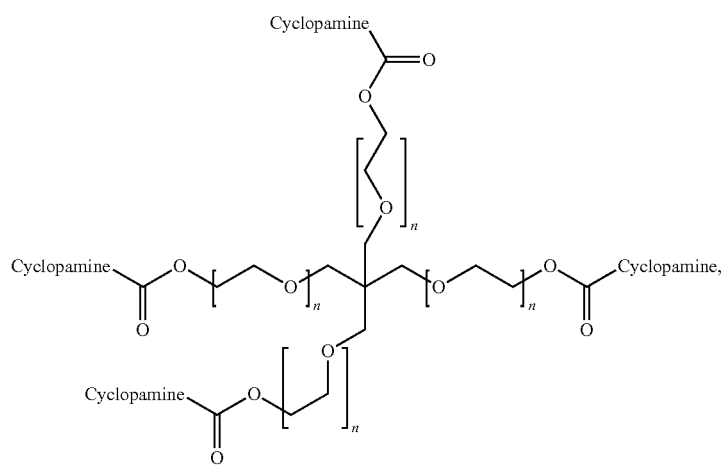
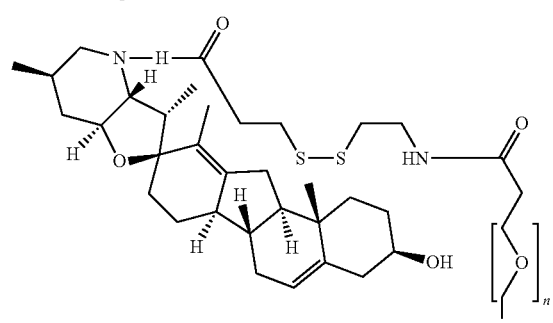

-continued
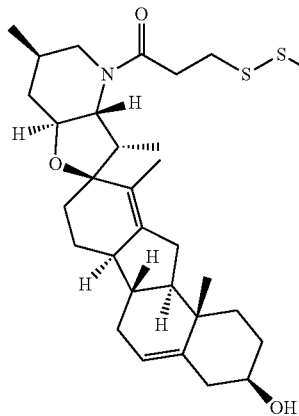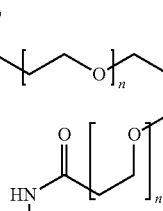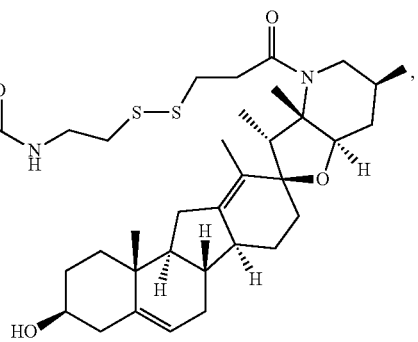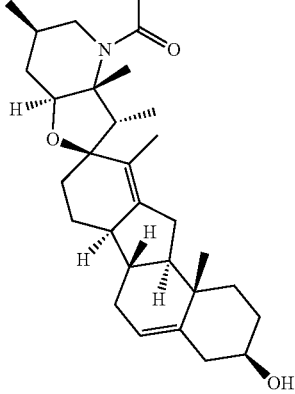
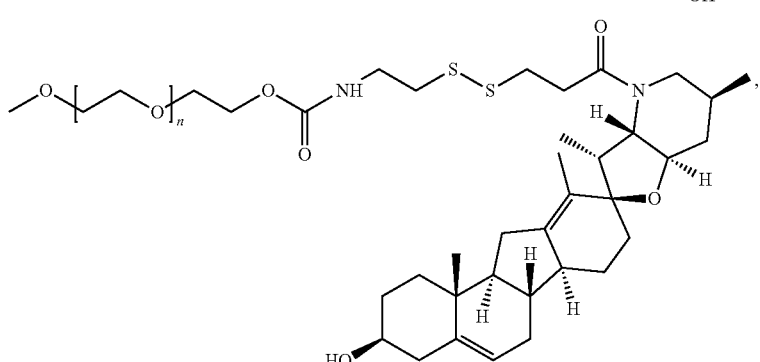
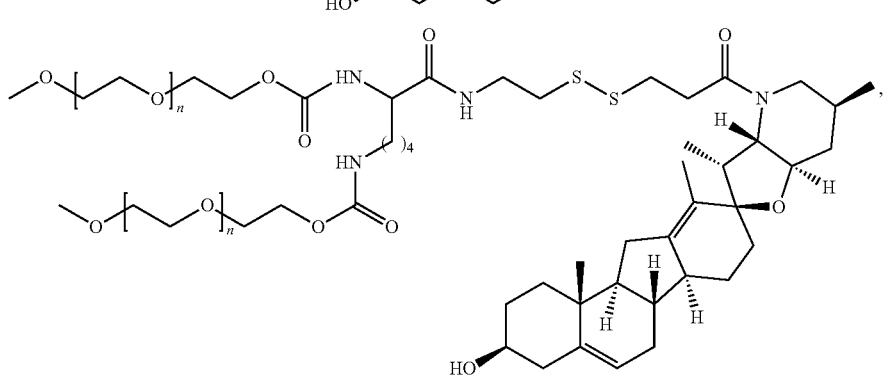

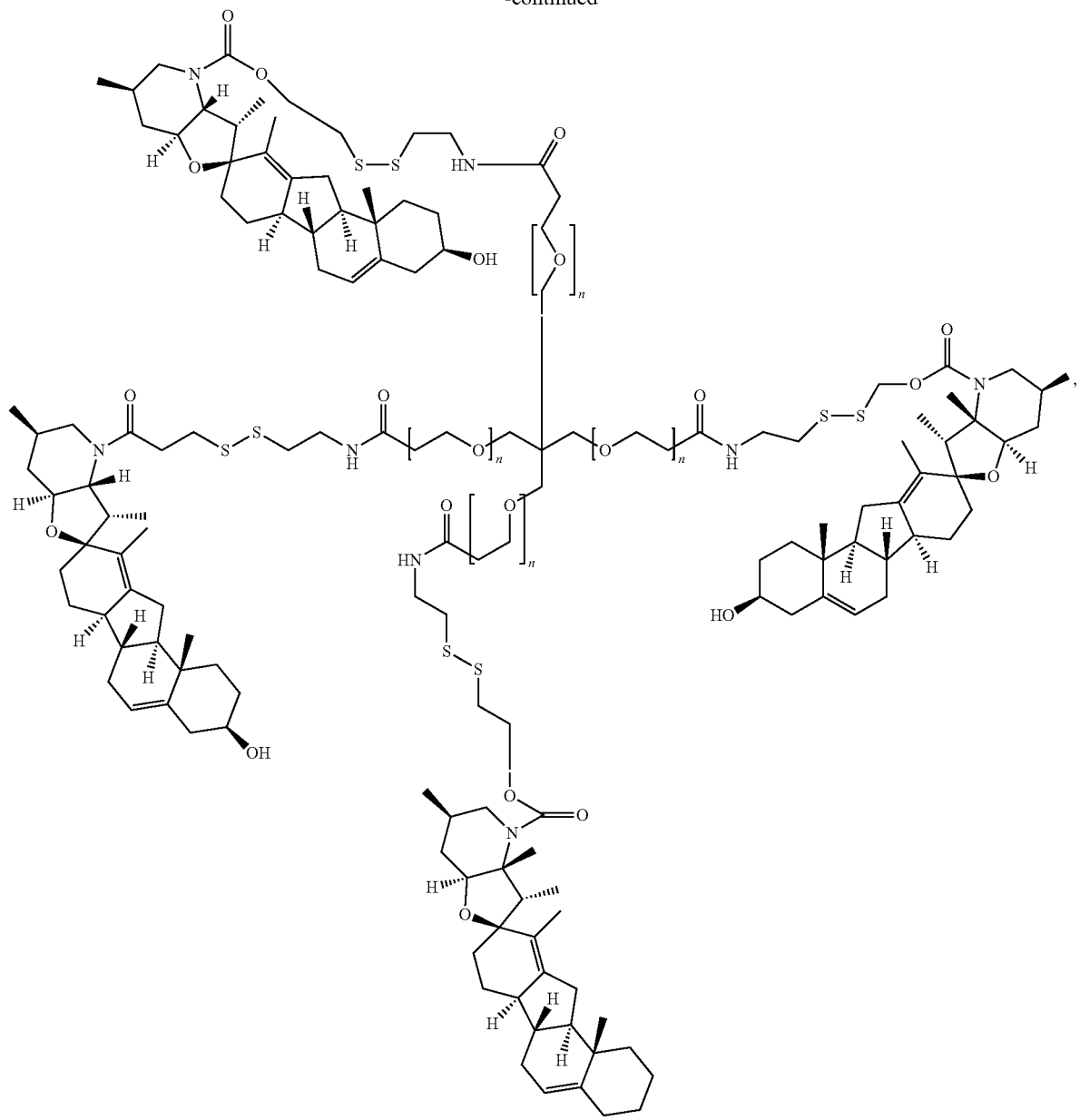

and a pharmaceutically acceptable salt thereof,
wherein n at each occurrence is independently an integer of 100 to 4500.

6. A method for preparing the PEGylated cyclopamine analog according to claim 1, comprising the following steps:
   i) providing polyethylene glycol;
   ii) reacting the substance provided in step i) with cyclopamine or a single enantiomer thereof, a mixture of enantiomers, or a mixture of diastereomers, or a pharmaceutically acceptable salt thereof to obtain a PEGylated cyclopamine analog, and, optionally,
   iii) subjecting the PEGylated cyclopamine analog obtained in step ii) to separation, crystallization, purification, salification, or solvation.

7. A pharmaceutical composition, comprising a therapeutically effective amount of the PEGylated cyclopamine analog according to claim 1, or a single enantiomer thereof, a mixture of enantiomers, or a mixture of diastereomers, or a pharmaceutically acceptable salt thereof, and optionally one or more pharmaceutically acceptable carriers or excipients.

8. The pharmaceutical composition according to claim 7 wherein the therapeutically effective amount is an amount effective for the treatment of proliferative diseases, neoplastic diseases or cancer diseases, wherein the proliferative diseases, neoplastic diseases, or cancer diseases are colon cancer or ovarian cancer.

9. A method of treating proliferative diseases, neoplastic diseases or cancer diseases in a mammal in need, which comprises administering to the mammal in need a therapeutically effective amount of the PEGylated cyclopamine analog according to claim 1, wherein the proliferative diseases, neoplastic diseases, or cancer diseases are colon cancer or ovarian cancer.

10. The PEGylated cyclopamine analog according to claim 3, wherein $R_1$ is $C_{1-8}$ alkyl, $C_{1-6}$ alkyl, or $C_{1-4}$ alkyl.

11. The PEGylated cyclopamine analog according to claim 4, wherein (1) R is straight or branched polyethylene glycol having a molecular weight of 400 to 160,000 Dalton, 500 to 150,000 Dalton, 600 to 120,000 Dalton, 800 to 100,000 Dalton, 1000 to 80,000 Dalton, 1,500 to 60,000 Dalton, 2,000 to 50,000 Dalton, 5,000 to 50,000 Dalton, 7,500 to 50,000 Dalton, or 10,000 to 50,000 Dalton.

12. The PEGylated cyclopamine analog according to claim 3, wherein $R_1$ is Me.

13. A pharmaceutical composition, comprising a therapeutically effective amount of the PEGylated cyclopamine analog according to claim 5, or a single enantiomer thereof, a mixture of enantiomers, or a mixture of diastereomers, or a pharmaceutically acceptable salt thereof, and optionally one or more pharmaceutically acceptable carriers or excipients.

14. The pharmaceutical composition according to claim 13 wherein the therapeutically effective amount is an amount effective for the treatment of proliferative diseases, neoplastic diseases or cancer diseases, wherein the proliferative diseases, neoplastic diseases or cancer diseases are colon cancer or ovarian cancer.

15. A method of treating proliferative diseases, neoplastic diseases or cancer diseases in a mammal in need, which comprises administering to the mammal in need a therapeutically effective amount of the PEGylated cyclopamine analog according to claim 5, wherein the proliferative diseases, neoplastic diseases or cancer diseases are colon cancer or ovarian cancer.

16. A compound having the following formula:

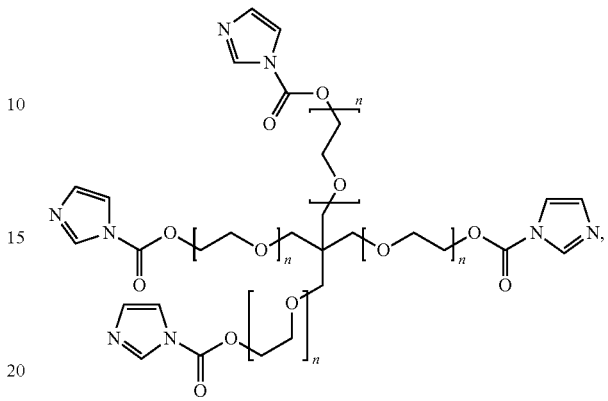

wherein n at each occurrence is independently an integer of 100 to 4500.

* * * * *

UNITED STATES PATENT AND TRADEMARK OFFICE
CERTIFICATE OF CORRECTION

PATENT NO.         : 8,877,928 B2
APPLICATION NO.    : 13/882797
DATED              : November 4, 2014
INVENTOR(S)        : Chun Song et al.

It is certified that error appears in the above-identified patent and that said Letters Patent is hereby corrected as shown below:

Title page, item (73) Assignee, under SHANDONG UNIVERSITY:
Please insert -- BEIJING KEMEDICINE CO., LTD --

Signed and Sealed this
Eleventh Day of October, 2016

Michelle K. Lee
*Director of the United States Patent and Trademark Office*